(12) United States Patent
Krug

(10) Patent No.: US 6,859,658 B1
(45) Date of Patent: Feb. 22, 2005

(54) DEVICE FOR NON-INVASIVELY DETECTING THE OXYGEN METABOLISM IN TISSUES

(75) Inventor: Alfons Krug, Biebertal (DE)

(73) Assignee: LEA Medizintechnik GmbH, Giessen (DE)

( * ) Notice: Subject to any disclaimer, the term of this patent is extended or adjusted under 35 U.S.C. 154(b) by 0 days.

(21) Appl. No.: 09/831,376

(22) PCT Filed: Nov. 18, 1999

(86) PCT No.: PCT/EP99/08864

§ 371 (c)(1),
(2), (4) Date: May 17, 2001

(87) PCT Pub. No.: WO00/28887

PCT Pub. Date: May 25, 2000

(30) Foreign Application Priority Data

Nov. 18, 1998 (DE) .......................... 198 53 028

(51) Int. Cl.⁷ ................................. A61B 5/00
(52) U.S. Cl. ..................... 600/323; 600/328
(58) Field of Search .................. 600/323, 322, 600/324, 325, 326, 327, 328, 329, 330, 332, 333, 334, 335, 336, 377, 342, 380

(56) References Cited

U.S. PATENT DOCUMENTS

| | | | |
|---|---|---|---|
| 4,515,165 A | * | 5/1985 | Carroll ....................... 600/475 |
| 5,131,391 A | | 7/1992 | Sakai et al. |
| 5,305,745 A | * | 4/1994 | Zacouto ....................... 600/324 |
| 5,524,617 A | | 6/1996 | Mannheimer |
| 5,564,417 A | * | 10/1996 | Chance ....................... 600/476 |
| 5,772,587 A | | 6/1998 | Gratton et al. |
| 6,246,892 B1 | * | 6/2001 | Chance ....................... 600/310 |
| 6,263,221 B1 | * | 7/2001 | Chance et al. .............. 600/310 |
| 6,312,393 B1 | * | 11/2001 | Abreu ......................... 600/558 |

FOREIGN PATENT DOCUMENTS

| | | |
|---|---|---|
| DE | 19640807 A1 | 9/1997 |
| DE | 19634152 A1 | 3/1998 |
| EP | 0771546 A2 | 11/1996 |
| GB | 2132483 | 7/1984 |
| WO | WO-96/39927 | 12/1996 |
| WO | WO-96/41566 | 12/1996 |

* cited by examiner

Primary Examiner—Daniel Robinson
(74) Attorney, Agent, or Firm—Charles P. Boukus

(57) ABSTRACT

The invention relates to an apparatus for noninvasive determination of the oxygen turnover and data derived therefrom with an optical sensor (S) to be placed on the tissue with one or more light sources (W, L) which send light through the optical fibers to the sensor (S), one or more detectors (DD, DR) which receive light backscattered by the tissue through optical fibers, and an evaluation unit.

11 Claims, 20 Drawing Sheets

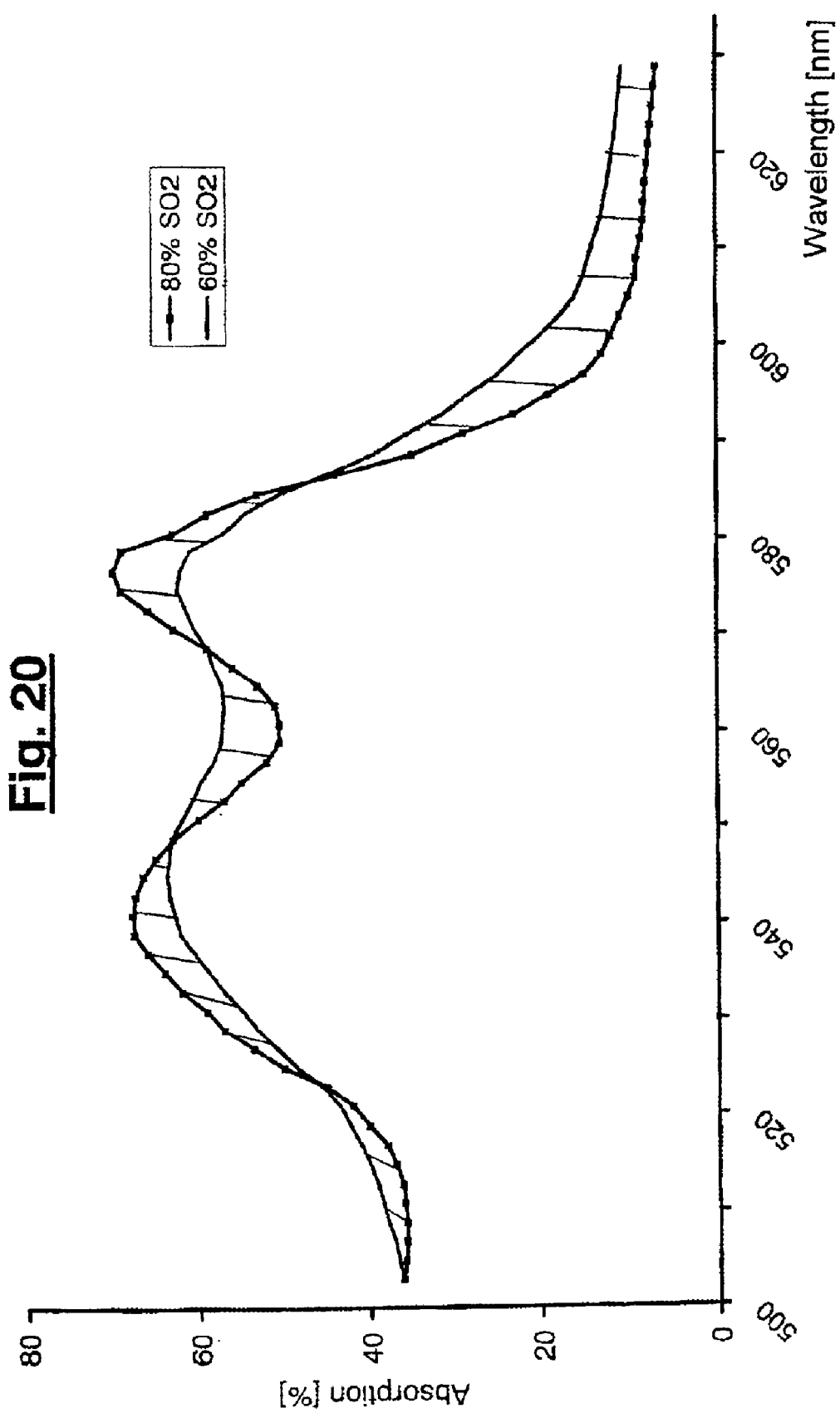

DEVICE FOR NON-INVASIVELY DETECTING THE OXYGEN METABOLISM IN TISSUES

DESCRIPTION

The invention relates to the determination of the local oxygen turnover, the oxygen consumption, the oxygen content and the locally transported amount of oxygen in perfused tissues using an optical sensor as set forth in the preamble to claim 1.

Oxygen is of elemental importance for almost all cells in biological tissues. In perfused tissues, oxygen is mostly transported in a form bound to hemoglobin, which is incorporated in the erythrocytes, from the lung to the oxygen-consuming cells. Arterial hemoglobin in the systemic circulation which has undergone saturation in the lung is almost 100% saturated with oxygen. In the peripheral tissue, the oxygen is then delivered along the capillaries to the cells. Correspondingly lower saturations of hemoglobin with oxygen are measured in the tissue regions at the venous end of the capillary and in the downstream venules and veins.

Noninvasive measurement of the oxygen content in tissue according to the prior art is possible only with very elaborate methods such as NMR (nuclear magnetic resonance). In addition, dynamic measurements of the oxygen consumption or monitoring of the oxygen removal through tissue respiration are not as yet possible with NMR methods.

The energy metabolism of the cells, which is closely linked to the oxygen uptake, can be determined only invasively, by taking samples of tissue or body fluids followed by biochemical laboratory analysis of the metabolic products. Thus, no dynamic measurements of the oxygen consumption or long-term monitoring are possible with these biochemical laboratory methods.

The arterial saturation of hemoglobin $SO_2$ (%) in the arterial system can be determined by so-called pulse oximeters, but these do not customarily allow the capillary-venous hemoglobin saturation levels, the hemoglobin concentration in the measured volume or the blood flow to be determined. The methods used in pulse oximetry are based on findings from cuvette photometry and use only a few individual wavelengths, so that a change in the measured volume and the recording of changes in scattering or absorption cannot be taken into account. This means that these measurement methods are associated with considerable measurement uncertainties. The advantage of these instruments to date is that they are very convenient and easy to handle.

Some spectrometric and spectroscopic methods are now known for determining the saturation of hemoglobin $SO_2$ [%] in the capillary venous system and the amount of hemoglobin in the measured volume (EMPHO, NIRO500, HemoSpec and newly AbTisSpec). These systems in some cases permit quantitative determination of the saturation of the hemoglobin with oxygen $SO_2$ [%]. By comparison therewith, determination of the amount of blood or the hemoglobin concentration in the capillary venous tissue bed is possible with said systems only in relative numerical measures. It is not possible with said methods to make a quantitative statement about the hemoglobin concentration in the measured volume or the amount of blood in the tissue, because these methods lack a relation to the detection region and thus to the light path, and lack depth selectivity.

Two methods offer a possible approach to quantifying the light path and thus the effective measured volume:

firstly so-called PMS (phase-modulated spectroscopy) and secondly TRS (time-resolved spectroscopy). These time-resolved methods have the crucial disadvantage, however, that they can operate with only a few wavelengths because of the need to use laser sources. It is thus possible to determine the saturation of hemoglobin with $O_2$, which is found from the change in spectral light absorption, only with difficulty and then only with very costly laser methods.

Laser Doppler methods such as, for example, the Opto-Flow can be used to obtain the blood flow rates and the amount of blood flowing as relative magnitudes. This class of optical methods based on evaluation of Doppler signals does not make it possible to gain information for determining the oxygen loading of the erythrocytes (the red blood corpuscles) or the current measured volume.

However, for a complete description of the state of oxygen supply in perfused tissues, it is necessary in addition to the parameter of blood flow rate also to determine by measurement techniques the amount of blood moved (number of red blood corpuscles moved), the total amount of blood in the tissue (also called the hemoglobin concentration) and the loading of the red blood corpuscles with oxygen (also called hemoglobin oxygenation or saturation $SO_2$).

EP 771 546 A2 discloses an apparatus for the noninvasive optical measurement of the blood flow in biological tissue.

The propagation of light in biological media, scattering suspensions, tissue sections and intact tissues and cell structures is determined by their optical properties. The propagation of light is moreover determined by the two basic phenomena of light absorption and light scattering. The absorption of light or the attenuation in the sense of converting the light energy into light of a higher wavelength takes place through interaction with cellular and subcellular structures of macromolecules and single molecules. A molecule which absorbs strongly in the visible region of wavelengths is, for example, the heme group in the hemoglobin molecule. Absorption causes visible light to lose part of its intensity on the light path through the tissue. The absorption measurements of the invention relate primarily to hemoglobin, the red blood pigment, which is also the strongest absorber in the visible wavelength region in virtually all tissues.

In contrast to this, light loses no energy through elastic scattering. The incident electromagnetic wave which interacts with the scattering center radiates the energy again, after excitation by the incident light wave, into the various spatial angles. During this, the light retains its wavelength, and only the direction of propagation of the light is altered by the scattering centers. At the molecular level, the physical process is to be conceived as excitation of the scattering particles by the incident light wave and thereafter emission of the energy back into space at the same wavelength. The directions in which the light energy is radiated then depend on the geometry, the shape and the electromagnetic distribution of the electron shells of the molecule, and on the structure.

The incident, directed beam is converted on the path through the tissue into diffuse radiation and adds up to forward scattering of the excited scattering centers. After scattering, which is in some circumstances multiple, a small part of the incident light intensity returns to the surface. The radiation backwards from all the scattering centers adds up to the backscattering. The light guides on the organ surface can detect only light which has been backscattered and not quenched by absorption on its light path. However, the only light detected by the light guide on the organ surface is that backscattered within the light guide aperture. This conception of the propagation of light is formally described in the radiation transport theory.

It is an object of the invention to determine by measurement techniques the hemoglobin oxygenation and the hemoglobin concentration, and measurements derived therefrom, and to propose an instrument for measuring the oxygen content and other related parameters (see Table 1).

This object is achieved according to the invention by an apparatus having the features of claim 1. Dependent claims relate to embodiments of the invention. A suitable name for the instrument according to the invention would be AbTisSpec, an acronym for absorption tissue spectrophotometer.

Thus, the invention proposes an apparatus which determines the oxygen content and data derived therefrom using an optical sensor to be placed on the tissue. It comprises one or more light sources which send light through optical fibers to the sensor, one or more detectors which receive light backscattered by the tissue through optical fibers, and an evaluation unit which obtains information about the oxygen content from the backscattered light. An apparatus of this type is described for other purposes for example in EP 771 546 A2, the whole of the disclosure and technical design of instruments of which is here made subject-matter of the invention.

The light source preferably used is a white light source and/or a laser source. Whereas the white light source introduces the light into the tissue whose backscattered portions later undergo spectral analysis, the laser light source introduces a monochromatic light whose backscattered portion has a measurable frequency shift so that a Doppler measurement and thus a rate measurement are possible.

A white light source (or various broad-band LEDs) is used for the illumination. A light source with a high illuminated field density and a spectrum of maximum whiteness and smoothness is crucial. The light backscattered from the tissue is spectrally analyzed by a polychromator, amplified and subsequently used as wavelength-dependent light intensity pattern for the evaluation.

The wavelength range from 500 to 650 nm (VIS) is particularly suitable for measurements close to the surface. By contrast, the wavelength range from 600 nm to 900 nm (NIR) is particularly suitable for depth-selective measurements even at relatively large depths because the effective depth of penetration of the light in the NIR wavelength range is greater than in the aforementioned wavelength range. In addition, different measured volumes are specified by the sensor geometry through different spacings of illumination and detection regions. The combination of the selection of detection spacings and appropriate wavelength ranges can thus be clearly defined and permits clear demarcation of individual measured volumes from one another. For calculation of the saturation values there is evaluation of the spectral shape of the spectra, for example by a shape recognition and mixing method or of an approximation of the diffusion equation. The measurements obtained according to the invention are, depth-selectively, the saturation of the hemoglobin with $O_2$ in the capillary venous tissue bed.

The measured volume is determined by a novel method, namely by measuring an intensity gradient on the surface in combination with determination of the absorption and scattering coefficients from the Doppler measurements, and of the spectrometric measurements.

The amount of hemoglobin can be obtained from the evaluation of the spectrometric data. The absorption caused by the attenuation of light by the hemoglobin is determined by a method whose bases are described for the first time by A. Krug, thesis, University of Erlangen-Nuremberg 1998.

A large number of measured quantities is required to describe the complete oxygen supply situation (see Table 1). The arterial saturation and, independently thereof, the capillary venous saturation of the hemoglobin must be determined. It is possible from the difference between the arterial saturation and the saturation of the hemoglobin in the capillaries, venules and veins then to determine the $O_2$ turnover or the oxygen uptake. Combination of this differential amount with the blood flow values affords the 0, consumption in the investigated tissue volume, which can thus be determined locally.

In summary, the following determination quantities must be measured to determine the local oxygen supply:
1. Depth-selectively the saturation of hemoglobin $SO_2$ [%] in the arterial system.
2. Depth-selectively the saturation of hemoglobin $SO_2$ [%]; in the capillary venous system.
3. Depth-selectively the amount of hemoglobin in the measured volume, from the absorption coefficients.
4. Size of the measured volume, resulting from the surface gradient measurement, the scattering coefficients and the anisotropy factors, or from models of the diffusion theory.
5. Depth-selectively the amount of blood flowing and the blood flow rate.
6. The local tissue temperature.

The combination of these measured quantities and the detection by an integrating sensor which guarantees measurements in the same area permits measurement of the local oxygen turnover of perfused tissue.

It is possible to provide as evaluation unit a spectrometer, a spectroscope, a laser Doppler spectroscope, a tissue spectrometer, a tissue spectroscope, a pulse oximeter and/or a temperature gauge, each alone or in any desired combination.

It is thus possible to determine
a) the local oxygen content,
b) the local oxygen consumption in arterial/venous mixed tissue,
c) the oxygen consumption rate in arterial/venous mixed tissue,
d) the total amount of blood,
e) the local oxygen transport capacity,
f) the locally transported amount of oxygen,
g) the oxygen turnover in arterial/venous mixed tissue,
h) the oxygen turnover rate in arterial/venous mixed tissue and/or i) the local tissue oxygen partial pressure in perfused tissues.

In one embodiment of the invention, information is obtained from different depths by the selection of the wavelength range and of the detector-transmitter separation. Thus, measurements can be obtained both from the tissue surface and from deeper regions.

The apparatus according to the invention is suitable not only for detection of hemoglobin and of the measurements which can be derived therefrom, but also for measuring the content of tissue pigments such as cytochromes, myoglobin, melanin, bilirubin or other pigments present in the tissue, and data derived therefrom. The same optical sensor can be used for placing on the tissue for this purpose. Likewise the one or more light sources which send the light through optical fibers to the sensor. In addition, one or more detectors which receive light backscattered from the tissue through optical fibers and pass it to an evaluation unit. The evaluation unit processes the received data appropriately and measures the pigment content, its distribution or its transport.

The light source which can be provided in this apparatus is also a white light source and/or a laser source.

It is likewise possible to provide as evaluation unit a spectrometer, a spectroscope, a laser Doppler spectroscope, a tissue spectrometer, a tissue spectroscope, a pulse oximeter and/or a temperature sensor, each singly or in any desired combination.

Information from different depths can be obtained by the selection of the wavelength range and of the detector-transmitter separation.

In another embodiment of the invention, a bundle of optical fibers which extends from the sensor to the detector or to a camera, such as a CCD camera, can be provided so that a two-dimensional image of the recorded measurements can be generated. This makes it possible to produce an extremely vivid image of the two-dimensional hemoglobin distribution and/or of the oxygen saturation and/or of the oxygen parameters, as shown in Table 1, and/or of the distribution of other pigments in or on the margin of a tissue.

On use of an additionally depth-selective sensor or of a depth-selective evaluation it is possible to generate a three-dimensional image of the recorded measurements. This permits a "view" into the interior of an organ or of a tissue and permits layer-wise representation of the relevant data.

Crucial for these optical measurements according to the invention is direct contact of the sensor with the organ surface. Only this makes it possible to carry out measurements of backscattered light instead of, for example, measurements of reflected light. Only when the sensor is in contact is it possible to carry out depth-selective measurements or else measurements related to the measured volume. For measurements of the microcirculation it is, of course, crucial to construct appropriate mechanical applicators which do not impair the microcirculation even in the capillary layer near the surface.

Further advantages, features and applications of the present invention are evident from the following description of a number of exemplary embodiments on the basis of the drawings. In this connection, all the features shown belong separately or in any combination to the invention, irrespective of their inclusion in the description or the claims.

They are shown in:

FIG. 1 an integrated sensor,

FIG. 2 application form of the sensor, integration of laser Doppler and tissue spectrometer, FIG. 3 application form of the sensor, integration of the laser Doppler and tissue spectrometer, FIG. 4 application form of the sensor, integration of tissue spectrometer and/or laser Doppler, FIG. 5 application form of the sensor, integration of tissue spectrometer and/or laser Doppler, FIG. 6 application form of the sensor, integration of the laser Doppler and tissue spectrometer, FIG. 7 a tissue spectrometer, FIG. 8 a bilayer model, FIG. 9 crude tissue spectra, FIG. 10 hemoglobin spectra, 0 to 100% oxygenated, FIG. 11 an ear sensor, FIG. 12 a secure sensor, FIG. 13 the extinction as a function of the hemoglobin concentration and oxygenation, FIG. 14 the extinction as a function of the hemoglobin concentration in tissue perfused in isolation, FIG. 15 backscattering functions in the x and z directions FIG. 16 a scattering cuvette, FIG. 17 detection depths, FIG. 18 transfer function of the x to z gradients, FIG. 19 the model of a measured volume, FIG. 20 two absorption spectra, FIG. 21 an apparatus for recording two-dimensional measurement distributions, FIG. 22 a two-dimensional measurement distribution, FIG. 23 an apparatus for recording three-dimensional measurement distributions and FIG. 24 cytochrome spectra, oxidized cytochromes and reduced cytochromes measured in a suspension of mytochondria.

FIG. 1 shows diagrammatically, viewed from below, that is to say starting from the tissue, one embodiment, merely by way of example, of an integrated sensor S or measuring head as can be used in the apparatus according to the invention. In this case it contains for the illumination the white light source W, the laser light source L and a plurality of detectors, where DD designates the detectors for Doppler signals and DR designates the detectors for backscattered intensities. The linear arrangement shown is merely by way of example. Many other arrangements are possible, with the detectors DR, which are more remote from the light source W, receiving light which has penetrated into deeper regions of the tissue and has been backscattered there, as described in EP 771 546 A2. A temperature sensor DT is additionally shown.

According to the invention, photons from a coherent monochromatic light source L and, preferably, additionally photons from one or more broad-band white light sources W are beamed through the integrated sensor system S into the tissue in a first region. The re-emerging photons are detected (DD, DR) at various distances from this first region. In spatial alternation there is detection of the light for the laser Doppler evaluation and for the spectroscopic or spectrometric evaluation. The design of the integrated sensor is depicted by way of example in FIG. 1.

The depth-selective laser Doppler measurements can be carried out with an apparatus as described in EP 771 546 A2.

According to the invention, FIG. 2 shows a specific form of the applicator used in particular for endoscopic measurements in the gastrointestinal region. The advantage of this fiber arrangement is the compact construction and easily reproducible geometry. As above, W represents the point of illumination with a white light source, and L represents the illumination with the laser source. In spatial alternation, the light is detected for the laser Doppler evaluation DD and for the spectroscopic or spectrometric evaluation DR. This sensor allows measurements in two detection depths in each case. The temperature sensor DT can optionally be arranged in the center of the sensor, or another fiber can.

FIG. 3 shows an arrangement from FIG. 2 which has been slightly modified according to the invention for applications with two separations for the laser Doppler measurements DD and evaluation DR of the spectrometric and/or spectroscopic measurements in one separation, but with larger total cross sections, because of the inclusion of the intensities of three detection fibers. FIG. 2 shows a white light source W and a laser light source L.

The fiber arrangement in FIG. 4 shows an apparatus according to the invention for determining the primary signals, obtained through a tissue spectrometer, of the arterial oxygen saturation, of the local oxygen saturation of the hemoglobin, and of the local hemoglobin concentration, as well as the parameters from Table 3. This arrangement has, because of the homogenous illumination of the central area by the six white light sources W, which are shown here by way of example, particular advantages of also being employable as reflection sensor. This apparatus is characterized in that the fibers W for illumination are located in a circle around the detector fiber DR. Light is transported into these fibers W via one or more light sources to the sensor S.

FIG. 5 shows a form, modified according to the invention, of the apparatus shown in FIG. 4 for the same applications mentioned therein, but for measurements with greater depths of penetration. The greater depths of penetration are achieved because the transmitter-detector separation is larger. It is also possible to combine the two apparatuses (FIG. 5 and FIG. 4) if the illumination sources are used alternately in relation to time or wavelength on a circular arrangement.

FIG. 6 is a modified form of the basis sensor from FIG. 1, in such a way that in each separation a whole line consisting of at least 2 fibers was arranged in place of one fiber in each case. This sensor permits integrating measurements in larger areas. The depth selectivity of the sensor from FIG. 1 is virtually retained.

FIG. 7 represents in principle the construction of a tissue photometer or tissue spectrometer. The core components are a broad-band light source W, optical fibers leading to the sensor S for illuminating the tissue, and optical fibers leading away from the sensor S for spectrally analyzed detection of the backscattered light from the tissue. The detection unit comprises a polychromator which both spectrally analyzes the light and quantifies in a wavelength-dependent manner the detected intensities. Thus, the tissue photometer makes available as initial values the color spectra which are subsequently used for the specific evaluations of the spectral information subsequent. In the design shown in FIG. 7 there is also a spectroscopic receiving unit which is connected in parallel with the polychromator and which makes it possible to pick up the detected backscattered intensities in a restricted wavelength range or at single wavelengths with greater speed and higher sensitivity. This detector unit is important for evaluating the pulsatile blood signals, for example for determining the arterial saturation of hemoglobin.

A white light source W (or various broad-band LEDs) for example are used for the illumination. A light source with high illuminated field density and a spectrum of maximum whiteness and smoothness is crucial. The light backscattered from the tissue is—spectrally analyzed by a polychromator —amplified and subsequently used as wavelength-dependent light intensity pattern for the evaluation.

The detector units necessary for detecting the hemoglobin levels near the surface have particularly high sensitivity in the visible wavelength range. The hemoglobin absorption values allow the hemoglobin levels to be determined to a maximum depth of 4 millimeters in the wavelength band from 500 to 650 nm.

According to the invention, two wavelength ranges are defined and distinguished.

The wavelength range from 500 to 650 nm (VIS) is particularly suitable for measurements near the surface, and the wavelength range from 580 to 900 nm (NIR) is particularly suitable for depth-selective measurements also at greater depths and in larger volumes, because the effective depth of penetration of the light in the NIR wavelength range is greater than in the aforementioned wavelength range. A detector unit which has particularly high sensitivity in the wavelength range near the infrared is necessary for detecting hemoglobin levels in the macrovolume. The hemoglobin absorption values in the wavelength range from 600 to 900 nm are a factor of 10 to 20 lower than in the visible wavelength range. Greater effective depths of penetration into the tissue are possible in principle owing to the reduced attenuation of light. In addition, different measured volumes are specified by the sensor geometry through different spacings of illumination and detection regions. The combination of the selection of detection spacings and appropriate wavelength ranges can thus be clearly defined and permits clear demarcation of individual measured volumes from one another.

Selective measurements near the surface are possible according to the invention firstly owing to the combination of the selection of the wavelength range from 500 to 650 nm and of the light guide separation of less than 2 mm. Secondly, measurements in the macrovolume and in great depths of detection are possible owing to the selection of the wavelength range from 650 to 900 nm together with light guide separations of more than 2 mm.

The detector unit with polychromator is the core of the tissue spectrometer according to the invention. A highest possible quantum yield and, resulting therefrom, a high detection frequency are desired. The greatest demands on the speed of detection are made on application of the method in cardiology, because the fastest physiological reactions are to be expected here. The saturation of hemoglobin $SO_2$ pulsates on the myocardium with the heart rate. The critical $SO_2$ values are to be expected at the end of systole because myocardial perfusion is greatly restricted during the contraction because of the high pressure in the ventricle. The heart rate is about 1/sec, with a systolic contraction duration in the region of 100 ms. This results in a maximally necessary scan frequency of 10 msec in order to be able to resolve this interval sufficiently. All the other physiological processes in the human body take place correspondingly slower and can be detected with lower scan frequencies. Another advantage of high scan rates is the increasing security of operation, which ensure "blur-free" recordings.

The following table summarizes the oxygen parameters for describing the local supply situation which are possible with the integrated sensor concept according to the invention. In the table, a cross has been put at the place at which a signal is required either from the tissue spectrometer values, the laser Doppler data, the pulse oximeter values or from the temperature values in order to be able to determine therefrom the corresponding oxygen parameter. The definition of the local oxygen supply quantities mentioned are explained in more detail hereinafter.

Thus, the measurement problem is divided into two different tasks. On the one hand, determination of the amount of hemoglobin $Hb_{amount}$ and, on the other hand, determination of the saturation of hemoglobin $SO_2$ with oxygen. Hüfner's number H produces the relationship between hemoglobin content and maximum oxygen content. Calculation of the amount of hemoglobin is described in turn in a following paragraph.

The oxygen turnover or the oxygen consumption in the tissue can be formally described by:

$$O_{2\ Consumption} = O_{2\ Constant\ arterial} - O_{2\ Content\ venous}$$

On the assumption that the amount of blood arterially and venously remains the same on the basis of the continuity equation, the formula can be simplified to:

$$O_{2\ Consumption} = H \cdot (Hb_{Saturationmaterial} - Hb_{Saturationvenous}) \cdot Hb_{Amount(in\ measured\ volume)}$$

It is known from the literature that the arterial blood volume in the tissue is typically less th an 5%. It is thus

TABLE 1

Compilation of the methods by which it is possible with use of the tissue spectrometer, the laser Doppler spectroscope, the pulse oximeter and/or a temperature gage to determine the clinically relevant blood and oxygen supply quantities on integration or partial integration of the sensors in a combined measuring head and integrative data analysis.

| | Tissue spectrometer | | | | Laser Doppler | | | Pulsoximeter | |
|---|---|---|---|---|---|---|---|---|---|
| Oxygen parameter | $SO_2$ cap.-ven. | $Hb_{conc}$ | Measured vol. or intensity gradient | $Hc_{conc/vol}$ | Blood flow | Velocity v | Pulsatility | $SO_2$ arterial | Temp. T |
| Oxygen content | X | | X | X | | | | | |
| Oxygen consumption | X | | X | X | | | | X | X |
| Total amount of blood | | | X | X | | | | | |
| $O_2$ transport capacity | | X | | | X | | | | |
| Amount of $O_2$— transported | X | X | | | X | | | | |
| Oxygen consumption rate | X | X | | | | | | X | X |
| Oxygen turnover | X | | X | X | | X | | X | X |
| Oxygen turnover rate | X | X | | | | | | X | X |
| Tissue $pO_2$ | X | | | | | | | | X |

The various oxygen parameters are derived, and the formal relationships of the methods according to the invention are defined, hereinafter.

Measurement of the oxygen content in the blood requires the amount of hemoglobin in the investigated tissue volume to be determined and the saturation of the hemoglobin present to be determined. It is therefore indispensable also to be able to determine quantitatively the illuminated tissue volume, because the amount of hemoglobin must be related to the value for the volume. The size of the illuminated or measured volume is crucially determined by the sensor geometry and the basic physical-optical parameters of the tissue, which are formulated in the form of absorption coefficients $\mu_a(\lambda)$ and scattering coefficients $\mu_s(\lambda)$ in the spectral range used of the light sources W and L. The relationships mentioned are derived in formal relations in the form of mathematical formulae stepwise below:

The $O_2$ content in the blood can thus be determined formally by the following formula:

$$O_{2\ Content} = Hb_{Amount} \cdot SO_2 H$$

sufficient to determine only the amount of hemoglobin in the capillary venous system without causing large errors.

If a restriction is made, in place of determination of the amount of $O_2$ which has been consumed, to the oxygen consumption rate, an indicator of the ratio of arterial to venous consumption, the following equation results therefrom for the determination:

$$O_{2\ Consumption\ rate} = (SO_{2\ arterial} - SO_{2\ venous}) \cdot Hb_{conc.}$$

The $Hb_{conc.}$ can be determined in the same manner as defined below. It is evident from the explanations hereinafter that $Hb_{conc.}$ is proportional to the extinction (or else the optical density) based on the particular measured volume.

It is not always possible in the tissue to combine the measured arterial saturation with the relevant capillary venous hemoglobin saturation. Strictly speaking, this is the case only when the continuity equation is satisfied in the appropriate tissue volume. It is thus important for arterial and capillary venous systems to be present in the measured volume under consideration and for the arterial pulse to be detectable.

However, it is possible to determine locally for every tissue volume a quantity which is to be referred to as the transported amount of oxygen or local oxygen transport capacity. These quantities can be measured with the novel integrated sensor concept.

The local oxygen transport capacity is determined by the number of moving erythrocytes locally present and their hemoglobin content, which is expressed by the locally moving hemoglobin concentration $Hb_{conc.}$ multiplied by Hüfner's number H and multiplied by the flow velocity $v_{blood}$ of the erythrocytes in the area investigated. Laser Doppler instruments which provide a spectral resolution of the velocity of the erythrocytes also provide a signal which reflects the amount of the moving erythrocytes ($amount_{erys,\ moving}$).

Since laser Doppler instruments calculate a value which corresponds to a relative perfusion Blood Flow, it is also possible in an approximate solution for relative values to employ the following equation. The blood flow in this case indicates a measure of the number of moving erythrocytes multiplied by their speed and thus represents a measure of a volumetric flow. The result is thus:

$$O_{2\ transport\ cap.} = \frac{H \cdot Hb_{conc.} \cdot \text{Blood Flow}}{Amount_{Erys,moving}}$$

The locally transported amount of oxygen is determined by the number of erythrocytes locally present multiplied by the flow velocity of the erythrocytes. This product is calculated by the laser Doppler instruments as a value which is referred to as blood flow. Blood flow multiplied by Hüfner's number and the local oxygen saturation of hemoglobin results in the transported amount of oxygen in the area investigated.

$$\text{Transported } O_{2\ Amount_{rel.}} = H \cdot SO_2 \cdot \text{Blood Flow}$$

The oxygen turnover is proportional to the amount of $O_2$ which is consumed in a defined area of tissue. The consumed amount of $O_2$ results from the difference between the amount of oxygen transported into the tissue (arterially) from the amount transported out again on the venous side. The quantitative oxygen turnover can be calculated as shown from:

$$O_{2_{turnover}} = (SO_{2_{arterial}} - SO_{2_{venous}}) \cdot \frac{H \cdot Hb_{Amount} \cdot v_{Blood} \cdot Amount_{Erys,moving}}{\text{in the measured volume}}$$

The same assumptions, approximations and abbreviations already assumed above apply in this case.

Since laser Doppler instruments calculate a value which corresponds to a relative perfusion Blood Flow, it is also possible in an approximate solution for relative values to employ the following equation.

$$O_{2\ Turnover\ rate} = (SO_{2_{aeterial}} - SO_{2_{venous}}) \cdot H \cdot \text{Blood Flow}$$

A description of the calculation of the primary information follows:

For calculation of the hemoglobin saturations $SO_2$ it is possible, for example, to analyze the spectral shape of the spectra by a shape recognition and mixing method. The measurements obtained are the saturation of hemoglobin with $O_2$ in the capillary venous tissue bed (described in W. Dümmler, Thesis, University of Erlangen, 1998).

In the present specific task of determining Hb spectra by tissue measurements, the absorption A is represented as total formed from the fundamental absorption $A_o$ and the combined absorption portions of 0% and 100% oxygenated hemoglobin. The spectral absorption coefficients are expressed by the specific extinctions of oxygenated Hb, $\epsilon_{ox}^{Hb}$ and deoxygenated extinction coefficients of Hb, $\epsilon_{deox}^{Hb}$ in the following equation:

$$A(\lambda) = A_o + C_{ox} \cdot \epsilon_{ox}^{Hb}(\lambda) + C_{deox} \cdot \epsilon_{deox}^{Hb}(\lambda)$$

The coefficients $C_{ox}$ and $C_{deox}$ indicate the combination portion from which each measured spectrum can be composed according to its degree of oxygenation.

The scattering S is approximated in a first approach as a first order wavelength-dependent function consisting of the linear combination of fundamental scattering $S_o$ and wavelength-dependent scattering portion $S_1$.

$$S(\lambda) = S_o + \lambda \cdot S_1$$

The method described above is used to bring the measured spectra to the form A/S and equate them to the model approach, see right-hand side of the following equation.

$$\frac{A}{S} = \frac{A + C_{ox} \cdot \varepsilon_{ox}^{Hb}(\lambda) + C_{deox} \cdot \varepsilon_{deox}^{Hb}(\lambda)}{S_0 + \lambda \cdot S_1}$$

The hemoglobin saturation is determined by iterative determination of the coefficients $$\frac{A_o}{S_o}, \frac{C_{ox}}{S_o}, \frac{C_{deox}}{S_o}, \frac{S_1}{S_o}$$

by Newton's and the least squares methods and subsequent quotient formation:

$$SO_2 = \frac{C_{ox}}{C_{ox} + C_{deox}}$$

The hemoglobin saturation can thus lie only in the range of values from 0% to 100%. The accuracy of calculation depends on the quality of the tissue model. The tissue model presented above can be extended at any time, and it is thus possible to replace the basic absorption $A_o$ by tissue-specific basic spectra $A_{Tissue}(\lambda)$ which can be taken from an organ table.

At the start of each measurement, in order to improve the spectrometer values a dark spectrum should be recorded in order to establish the electronic zero of the amplifier and the level of extraneous light incident on the detector unit. It is necessary secondly to record a spectrum over a white standard in order to be able to establish the instrument function of the lamp, of the sensor and of the complete detector unit. Depending on the quality of the spectrometer, the spectral accuracy should be carried out at defined time intervals by a spectral control measurement, for example using a mercury argon calibration source. The described balance spectra should preferably be recorded with an average rate which is at least 10 times high er than the subsequent tissue spectra, because the errors in the dark spectrum and in the white standard spectrum are passed on through the spectral preprocessing to all the measured data.

The recorded crude spectra must be preprocessed before they can be used for the evaluation. The backscattered spectrum $R(\lambda)$ is composed of:

$$R(\lambda) = \frac{Spectrum_{crude}(\lambda) - Spectrum_{dark}(\lambda)}{Spectrum_{white\ standard}(\lambda) - Spectrum_{dark}(\lambda)}$$

For this purpose, the spectrometer must run through a calibration routine, during which the dark spectrum and the white standard spectrum are recorded. The preprocessing of the spectra eliminates the chromatic errors of the optical system of the instrument in accordance with the prior art.

To calculate the hemoglobin oxygenation in the VIS and NIR region, completely oxygenated hemoglobin spectra $\epsilon_{ox}^{Hb}(\lambda)$ and completely deoxygenated hemoglobin spectra $\epsilon_{deox}^{Hb}(\lambda)$ are required. The spectra should be recorded with the same wavelength resolution with which the measured spectra are also digitized. The tissue model presented by W. Dümmler (Thesis, University of Erlangen, 1998) can be extended according to the invention so that the specific organ spectra $A_{tissue}(\lambda)$ are included directly in the model.

$$\frac{A}{S}(\lambda) = \frac{A_{tissue}(\lambda) + C_{ox} \cdot \varepsilon_{ox}^{Hb}(\lambda) + C_{deox} \cdot \varepsilon_{deox}^{Hb}(\lambda)}{S_0 + \lambda \cdot S_1}$$

The specific tissue spectra can be obtained for each organ as a typical average spectrum during hemoglobin-free perfusion.

It has been realized from many measurements that backscattered hemoglobin spectra are distorted by erythrocytes and, in particular, compressed compared with spectra recorded in the transmission configuration of light source and detector. The properties of the individual spectrometer components play no part in this. The amplitudes of the hemoglobin spectra measured in the reflectance configuration should be similar to the amplitudes of the Hb/HbO$_2$ reference spectra. This again means that suitable and comparable Hb/HbO$_2$ reference spectra are required in each case. The main reason for the compression of the spectra lies, according to the current state of knowledge, in the differences of the measured volumes of the various hemoglobin absorptions. Light with wavelengths between 540 nm and 580 nm experiences greater attenuation than in the adjoining wavelength ranges and therefore penetrates less deeply into the tissue. Light of the more weakly absorbing wavelengths of the hemoglobin spectrum by contrast penetrate more deeply into the tissue and therefore experience, in absolute terms, a greater degree of attenuation than would be concluded directly from the extinction. It was possible to conclude this relationship directly from the measurements of the depths of penetration in the bilayer models (see A. Krug, Thesis, Erlangen University, 1998).

A bilayer model which is composed of a scattering suspension (for example Intralipid®, cells or tissue layers) disposed on top of a total absorber, such as, for example, marking ink, separated by a PVC film only a few $\mu$m thick, is described in FIG. 8. Two light guides extend into the suspension; the first guides light in and the second picks up backscattered light. The arrangement is used for determining the 90% depth of penetration, which will also be referred to as the detection depth.

Examples of results of measurements of detection depths in Intralipid suspension are compiled in Table 2. The comparison shows that the detection depths determined at 542 nm are far smaller than at 628 and 760 nm, when hemoglobin modulates the measured volume because of its different absorption coefficients for the different wavelengths.

TABLE 2

Calculation of the detection depths, recorded with 200 $\mu$m quartz fibers in Intralipid suspension.

| Wavelength | 542 nm | 628 nm | 760 nm |
|---|---|---|---|
| Detection depths in $\mu$m for marking ink as background absorber | | | |
| IL 2% | 920 | 1000 | 1120 |
| IL2% + 0.25 g Hb/dl | 320 | 580 | 880 |
| Detection depths in $\mu$m for black PVC as background absorber | | | |
| IL 2% | 1000 | 1040 | 1060 |
| IL2% + 0.25 g Hb/dl | 380 | 660 | 920 |

It is possible in principle to take two routes for solving the problem of distortion of the backscattered Hb spectra. Either the measured spectra are rectified according to their hemoglobin concentration by relating the extinctions to the effective measured volume in each case, or a whole series of HbO$_2$ reference spectra are generated with different hemoglobin concentrations and different degrees of distortion and are made available to the evaluation algorithm. The former solution is to be preferred because, in this case, standard hemoglobin spectra from cuvette measurements can be used, and the determination of the measured volume can additionally be used for quantitative calculation of the hemoglobin concentration.

The amount of hemoglobin is determined as described in the literature by the following equation:

$$Hb_{Amount} = C_{HB} \cdot V_{Meo}$$

It is clear from the above formula that to determine the amount of hemoglobin it is necessary for the two quantities of the hemoglobin concentration $C_{Hb}$ (especially in the VIS) and the measured volume $V_{MEAS.}$ to be determined by measurement techniques and calculated.

Various theoretical approaches can be used to determine the amount of hemoglobin in the particular measured volume. In the simplest case, the hemoglobin concentration is determined using the Lambert-Beer law (see next formula):

$$Ext. = \log\frac{I_o}{I} = C_{Hb} \cdot \varepsilon_{Hb}(\lambda) \cdot d$$

The extinction Ext. is calculated from the logarithm of the light intensity $I_o$ beamed into the object, related to the light intensity I emerging from the object. According to Lambert-Beer, the extinction depends on the hemoglobin concentration $C_{Hb}$, the wavelength-dependent absorption coefficient $\epsilon_{Hb}$ and the cuvette path length d.

The $Hb_{conc.}$ is to be determined in the same manner as described above. $Hb_{conc.}$ is proportional to the extinction (or else the optical density) relative to the particular measured volume.

$$Hb_{conc.} = K_i \cdot \frac{OD}{V_{Meas.}} = K_i \cdot \frac{\log \frac{I_o}{I}}{\varepsilon_{Hb} \cdot V_{Meas.}}$$

Determination of the measured volume is described hereinafter.

Another possibility for determining the hemoglobin concentration is provided by the radiation transport equation. In its general form, however, no complete solution is possible and, for this reason, it cannot be manipulated particularly well. Therefore the diffusion approximation of the radiation transport equation is frequently used in tissue spectrometry.

The equations derived on the basis of the diffusion approximation are introduced below. Using the diffusion approximation, an x gradient in the reflectance configuration of the light guides is formally described as:

$$I(x) = \frac{3P_o}{16\pi^2} \cdot \frac{\exp\left(-x\sqrt{3\mu_o(\mu_o + \mu_s')}\right)}{x}(\mu_o + \mu_s')$$

From this it is possible by condensing to two coefficients $C_1$ and $C_2$ $$C_1 = \frac{3P_o}{16\pi^2}(\mu_a + \mu_s')$$
$$= \frac{3P_o}{16\pi^2}(\rho\sigma_a + \rho\sigma_s(1-g))$$

and $$C_2 = \sqrt{3\mu_a(\mu_a + \mu_s')}$$
$$= \sqrt{3\rho\sigma_a(\rho\sigma_a + \rho\sigma_s(1-g))}$$
$$= \rho \cdot \sqrt{3\sigma_a(\sigma_a + \sigma_s(1-g))}$$

to condense the description of the gradients to:

$$I(x) = C_1 \frac{\exp(-C_2 x)}{x}$$

From the coefficients $C_1$ and $C_2$ found it is possible subsequently to determine $\mu_a$ and $\mu_s$. The coefficient $\mu_a(\lambda)$ represents the absorption coefficient of the tissue, from which it is possible, with appropriate approximations or after neglecting other absorbers in the tissue, to determine the hemoglobin concentration in the tissue.

Quantitative determination of the local hemoglobin concentration in the microvolume by evaluating the backscattered spectra is a complex task. Various research groups have investigated the optical properties of various tissues. It has emerged that the scattering coefficient $\mu_s$ is at least 10 times larger than the absorption coefficient $\mu_a$. Accordingly, the backscattered amount of light is primarily determined by the scattering properties of the tissue investigated.

FIG. 9 shows three spectra, namely the spectrum of the instrument function $I_{inst.}(\lambda)$, the spectrum of an ideal scatterer $I'_o(\lambda_i)$ and a measured hemoglobin spectrum $I_m(\lambda_i)$.

The two statements which follow are important for developing the subsequent determination method for calculating the hemoglobin concentration:

1. The only light intensities which can be measured on the tissue surface are those reflected back by scattering in the tissue.
2. If there is an absorber such as hemoglobin in the tissue it attenuates the light on the path into the tissue between the scattering events and on the path back to the detector light guide.

It is possible to conclude from the two statements that, at a wavelength at which the absorption is negligibly small, the measured light intensity is determined only by the backscattering. At all other wavelengths where the absorption is not negligible, the light is attenuated by the absorber, and the intensity is therefore less than the undisturbed backscattered intensity.

Thus, a novel evaluation method for determining the Hb amplitudes of tissue spectra has been developed according to the invention. The first part has already been published in the thesis by A. Krug (1998, Erlangen University). The method in which the intermediate results of the Hb determination are related, by extracting hemoglobin amplitudes from the backscattered spectra, to the value for the measured volume, described by a second method, at the same measurement point is novel. This results according to the invention in hemoglobin concentrations which are continually related to the current measured volume. The intermediate value of the relative hemoglobin concentration can also be found from solutions of the diffusion equation.

FIG. 9 depicts uncorrected spectra. The curve $I_{inst.}(\lambda_i)$ shows the instrument function or the optical error function of the tissue spectrometer. All measured spectra must be corrected by comparison with this spectrum in order to eliminate the instrument-specific falsifications of the measured spectra.

The curve $I'_0(\lambda_i)$ corresponds to the spectrum obtained with a white scatterer. The curve $I_m(\lambda_i)$ corresponds to an actually measured spectrum obtained with a physiological hemoglobin concentration in the scattering medium.

If the pure backscattered intensity $I'_o(\lambda_i)$ is known, the proportion of light attenuation by the absorber can be found from the difference between the pure backscattered intensity and the measured intensity $I_m(\lambda_i)$. The formal relationship can be expressed by $$I'_0(\lambda_i) = I_m(\lambda_i) + \Delta I_{Abs}(\lambda_i)$$

The unattenuated backscattered intensity $I'_o$ is obtained in backscattering photometry if the absorber concentration in the tissue equals zero. That is to say if only scatterers are present in the tissue.

FIG. 10 shows a hemoglobin spectrum $I_m(\lambda_i)$ with oxygenation values from 0 to 100%, calculated by the color mixing method for determining the areas of the hemoglobin amplitudes. The assumption that a wavelength exists, at which the absorption by hemoglobin is negligibly small exists at wavelengths greater than 640 nm. The wavelengths of the absolute minima of the hemoglobin extinctions would be even more suitable, which are at 690 nm for oxygenated and at 850 nm for deoxygenated hemoglobin.

FIG. 10 illustrates that the difference between $I'_0(\lambda_i)$ and $I_m(\lambda_i)$ corresponds to the absorption of light at this wavelength. Thus, the quotient $$\log[I'_0(\lambda_i)/I_m(\lambda_i)]$$

also corresponds to the absorption. If this quotient is found, it represents a quantitative measure of the extinction or of the absorption of light in this ideally scattering medium.

To calculate the hemoglobin concentration, the area of the extracted hemoglobin amplitudes is integrated, and an absorption is calculated therefrom for each spectrum. The integrated for values of oxygenated and deoxygenated spectra differ, however. For this reason, in the second stage of development, an oxygenation-dependent correction of the extracted hemoglobin amplitudes or of the area absorptions was introduced. The basic idea of this correction is to establish the areas of the differently oxygenated spectra and to carry out a correction for the different levels of oxygenation. It was found that the area of a fully oxygenated Hb spectrum, for example in the wavelength range 500–630 nm is 16% larger than the area of a fully deoxygenated spectrum (see FIG. 10). The spectra in the literature, of Assendelft, 1970, were used to establish these corrections.

It was also possible, by calculations with a color mixing method, to establish the areas of all the intermediate levels of Hb oxygenation between the values of 0% and 100% $HbO_2$. The area of the tissue spectra is found after they are determined in a normalizing step independent of the level of hemoglobin oxygenation.

FIG. 11 shows an application of the optical oxygen sensor according to the invention together with a temperature sensor as ear sensor. FIG. 11 shows the auditory canal into which this special sensor head has been introduced, with eardrum. It can, for hygienic reasons, be provided with a transparent protective film. This hygienic cap and the sensor have a special shape adapted to the auditory canal and a type of mechanical stop which prevents perforation of the eardrum. The length of the sensor up to the mechanical stop is about 25 mm. An optical oxygen sensor as shown in FIG. 1 to FIG. 6 or FIG. 21 or else FIG. 23 is present in the sensor head. Measurement of the oxygen saturation in the eardrum, a planar structure, is crucial in this case. The combination with a temperature sensor provides the physician with the information he requires.

The temperature measurement methods which are suitable and preferred here are non-contact methods such as infrared temperature measurement, or the methods for temperature measurement in the space of a closed auditory canal or the inner ear by NTC or similar temperature measurement methods.

Since in this application form the optical oxygen sensor measures only in the membrane of the eardrum, which can be considered to be a two-dimensional structure, it is possible in this specific case to carry out a reflection measurement in place of a backscattering measurement as with measurements directly on organ surfaces. For this reason, non-contact infrared temperature measurement is to be preferred to an NTC sensor.

For optical measurements of the perfusion parameters also in a microvolume it is important to develop appropriate applicators which, on the one hand, guarantee that the sensor lies on and is thus in direct contact with the tissue and, on the other hand, permit a determination when the contact pressure on the tissue is too high. The contact pressure must not exceed a certain level because, otherwise, the perfusion of the capillaries near the surface is impaired by the pressure of the sensor and thus may lead in some circumstances to an incorrect measurement.

Suitable temperature sensors are non-contact methods such as infrared temperature measurement, or methods for temperature measurement in the space of the closed outer ear or NTC or similar temperature measurement methods.

In the embodiment of the applicator shown in FIG. 11, only reflection measurements are possible because the applicator is not in contact with the eardrum. Single-channel measurements with the tissue spectrometer, with the pulsatile tissue spectrometer, with the pulse oximeter, with the laser Doppler and/or the temperature probe are sufficient for reflection measurements.

For imaging tissue parameters on the eardrum, in accordance with FIG. 21 or FIG. 23, the ear stopper must be extended and must be placed directly on the eardrum. For 2D and, in particular, 3D imaging it is again necessary to carry out backscattering measurements in place of reflection measurements.

FIG. 12 shows an embodiment of a novel sensor head. For this, a sensor head as shown in FIG. 1 to 6, FIG. 21 or FIG. 23 is additionally integrated into a unit which makes it possible to detect simultaneously whether the sensor is reliably in contact with the tissue and whether the contact pressure of the sensor is not too high, and thus represents a pressure indicator.

This unit can be referred to as a secure sensor applicator. It comprises a groove which is 1 to 2 mm wide and in which two pairs of light guides are opposite one another on each side of the groove. On one side two transmitting fibers, on the other side two detecting fibers. The transmitted light from each transmitting fiber is preferably amplitude-modulated with a different frequency in each case. This amplitude modulation makes the secure sensor applicator secure against interference by foreign light sources and, moreover, permits separation of the light intensities coming from the two transmitting fibers. If the sensor is applied with the correct pressure, only a light attenuation is measured in channel 1, whereas no attenuation is yet detectable in channel 2. If the tissue is deformed too much due to the contact pressure being too high, this leads to increased bulging of the skin or of the tissue surface into the groove of the sensor, leading to channel 2 also then experiencing an attenuation of light transmission. It thus signals that the application pressure is too high and serves to establish that the measurement conditions are impermissible and would lead to reduced capillary perfusion.

Figure 13:
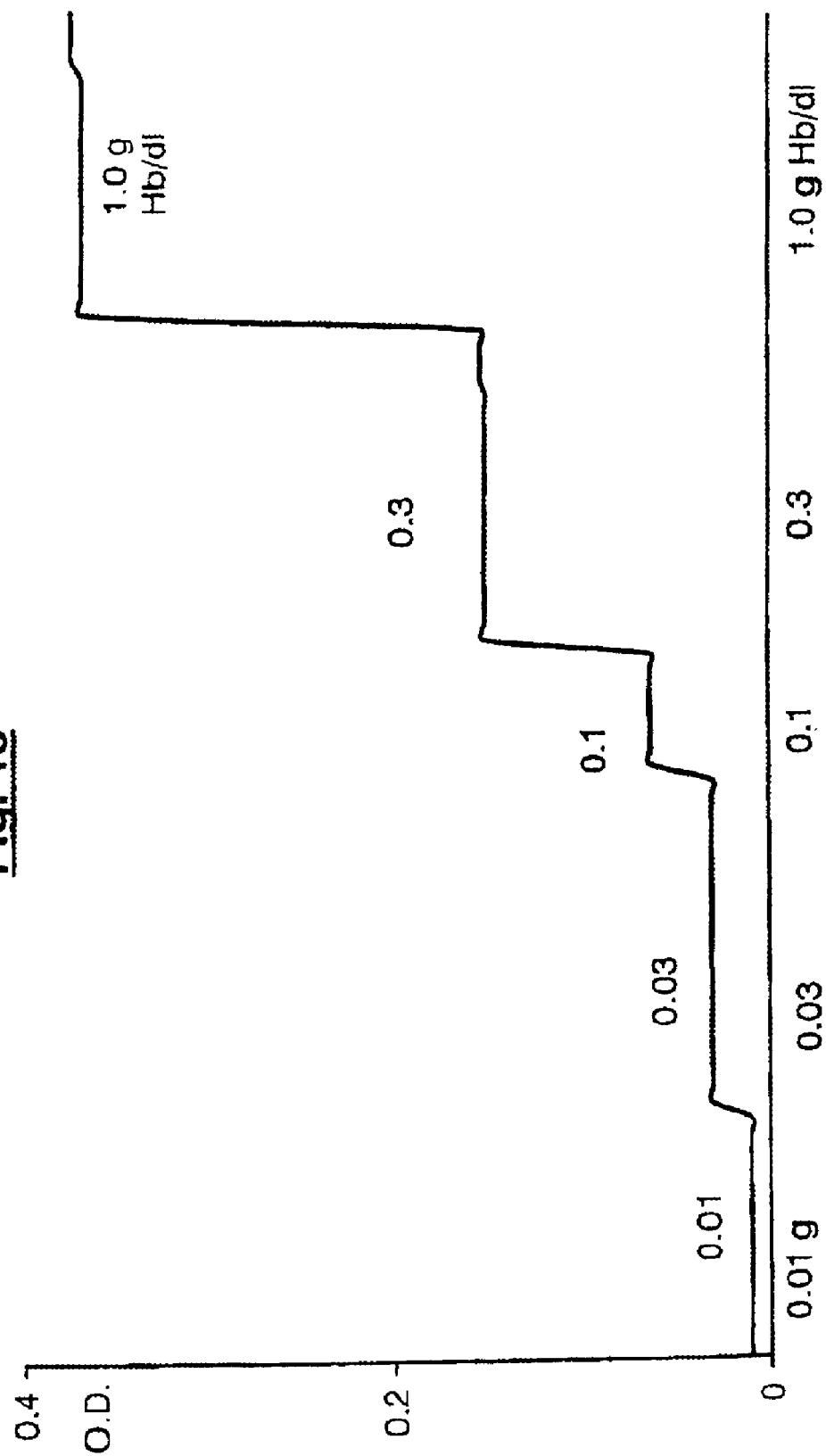
FIG. 13 shows the calculated relative extinctions (O.D.) at 5 different Hb concentrations.
Figure 14:
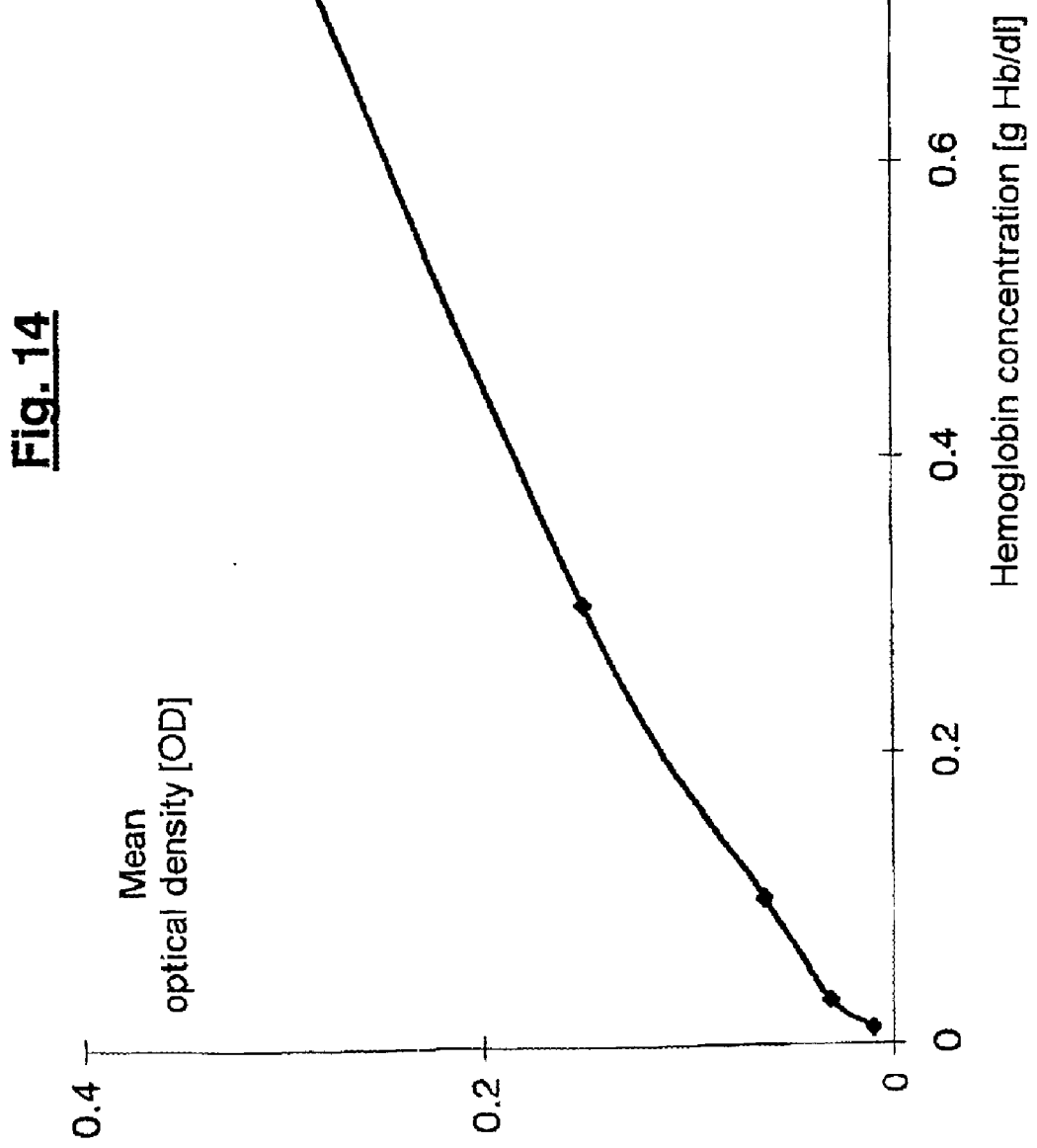
FIG. 14 shows the functional relationship between the hemoglobin concentration in a suspension and the calculated average relative extinctions (O. D.).

The two FIGS. 13 and 14 summarize the results of an experiment and document the validity of the method presented. The results indicate the relationship between Hb concentrations pipetted into the suspension and the oxygenation-dependent corrected Hb extinctions. The accuracy of the oxygenation-dependent correction for all hemoglobin concentration levels can be read off from FIG. 13 for changes in oxygenation from 09 to 100% $HbO_2$. The largest difference can be read off at 1.0 g/dl.

The method for calculating the relative hemoglobin concentration $Hb_{conc}$ in the NIR is to be designed in a similar way to that developed for the visible wavelength range. However, account must be taken of the particular spectral characteristics in the NIR. The selection of the wavelength range considered is crucial for the calculations with the Fitt algorithm because the Fitt algorithm can be applied only if there is an appropriately characteristic spectral difference depending on the hemoglobin oxygenation. It has emerged that the wavelength range 600–900 nm is particularly suitable for measurements in the NIR wavelength range.

Figure 15:
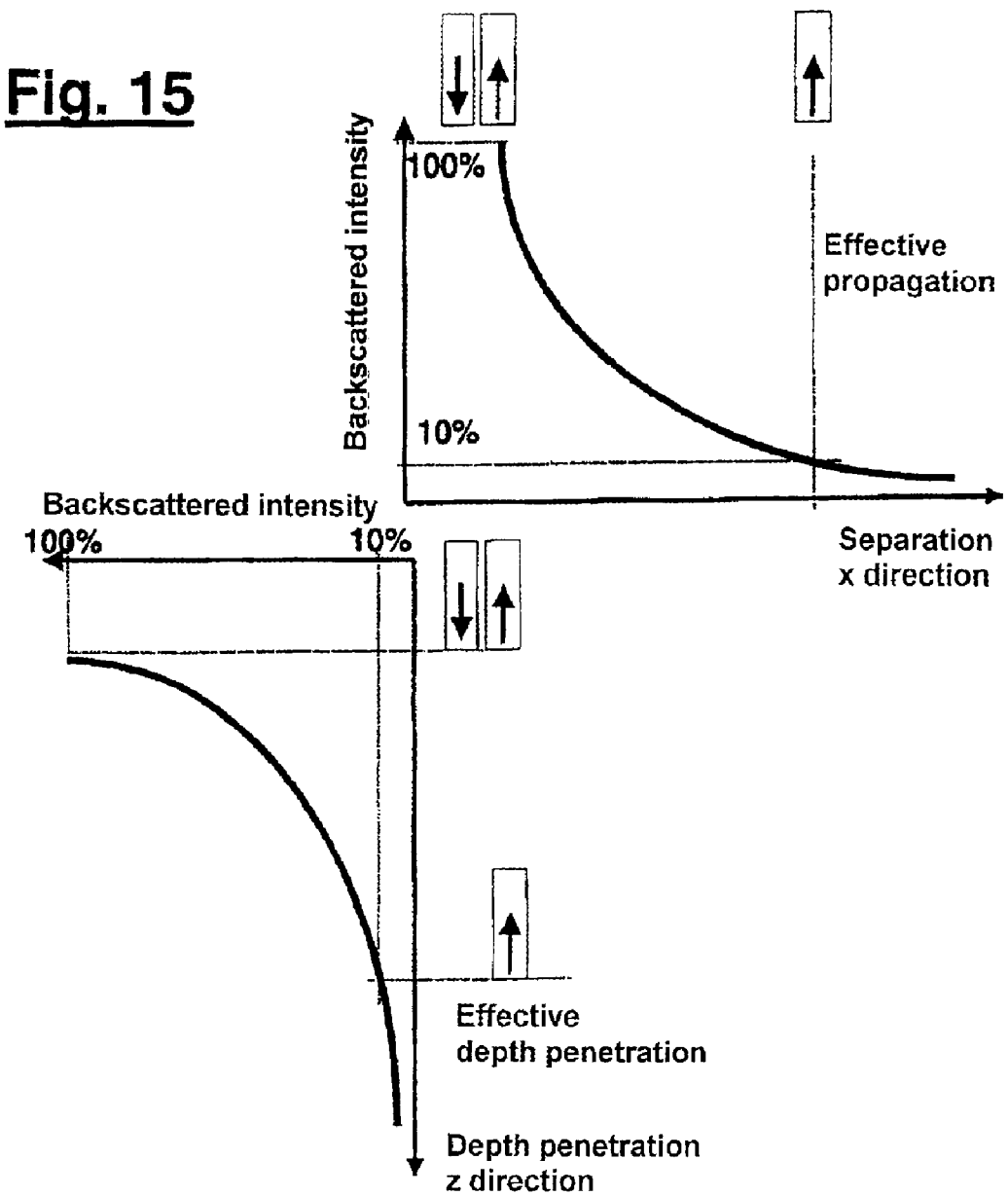

FIG. 15 shows the dependence of the backscattered intensity on the one hand on the transmitter-detector separation (x gradient) and on the depth of penetration (z gradient). The x gradient of the backscattered intensities as a function of the transmitter-detector separation and the z gradient can be determined in a scattering cuvette as shown in FIG. 16 without marking ink.

Figure 16:
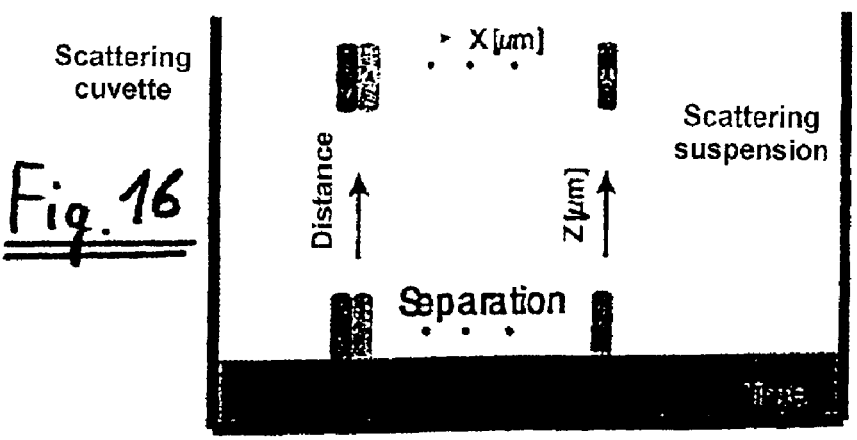

The effective depth of penetration, also referred to as detection depth herein, can be determined by the unit shown in FIG. 16 (see A. Krug, Thesis, Erlangen University, 1998).

FIG. 16 shows a scattering cuvette filled with scattering let suspension and marking ink for definition with depiction of the scanning directions. A new light guide separation z was set with a micrometer screw in each case and was then scanned in the x direction. The scan represents the light intensities of the various distances from the light guides to the marking ink—the "black hole".

Figure 17:
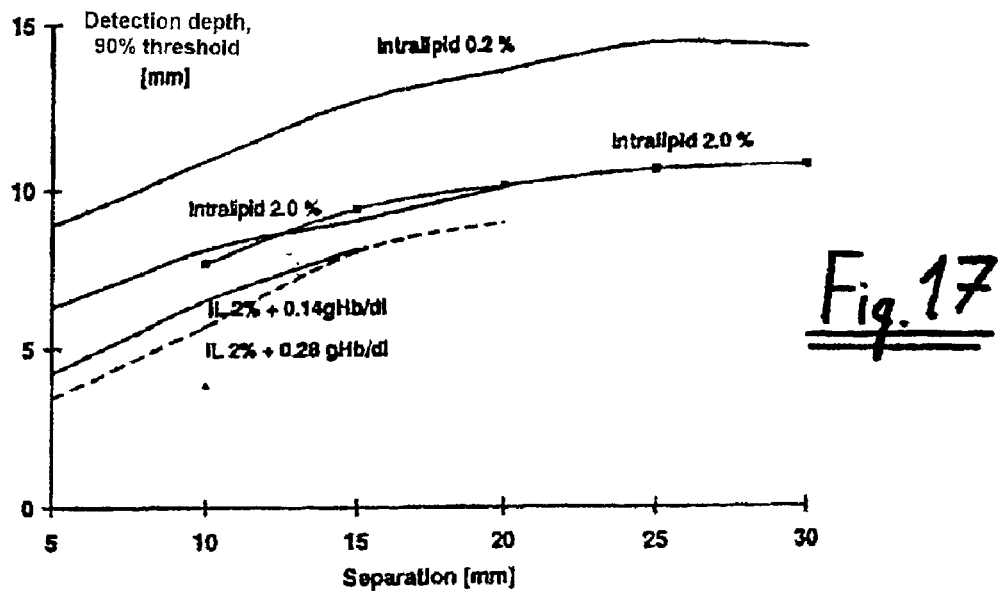

FIG. 17 shows a survey picture of calculations of detection depths using a 90% threshold in various Intralipid suspensions and with various separations, evaluated at 760 nm.

Now to the description of the calculation, which is novel according to the invention, of the current measured volume in the VIS and in the NIR: the measured volume $V_{meas.}$ can be determined from the measurement of a surface intensity gradient. In addition, a transfer function which must be determined experimentally for the particular tissue is required.

Figure 18:
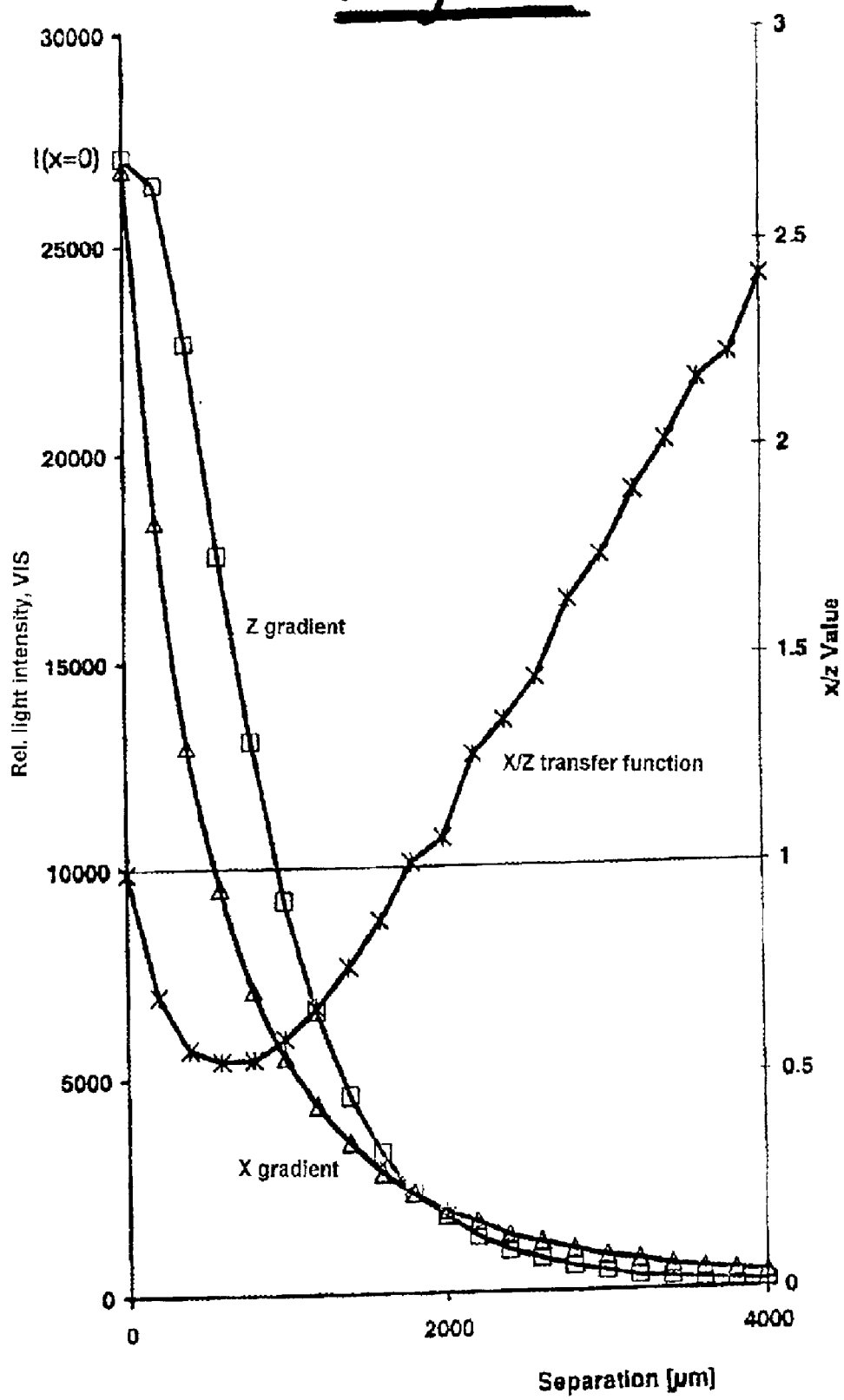

As is to be seen in FIG. 18, the transfer function produces the relationship between the intensity gradient on the surface, which can be established by measurement techniques, and the unmeasurable intensity gradient in the depth of the tissue. The effective measurement volume is regarded as being the volume in which the backscattered intensity gradients have been 90% attenuated, as shown in FIG. 15. The transfer function can be formally described by:

$$I_{z\ gradient}(z) = \text{transfer function}^{-1} * I_{x\ gradient}(x)$$

Figure 19:
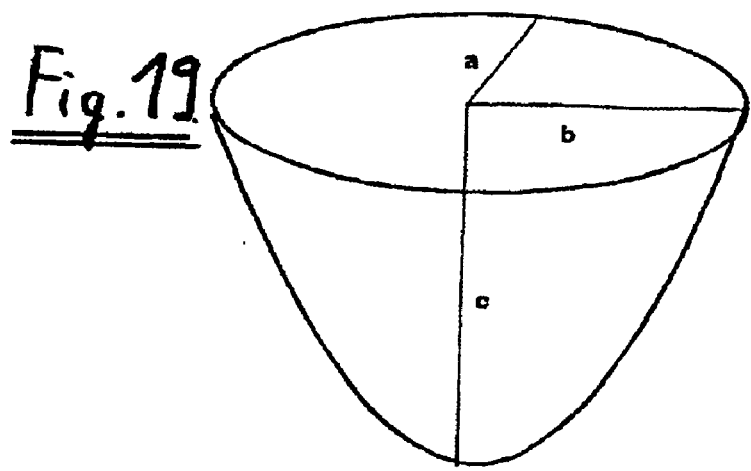

FIG. 19 shows the definition of the determination quantities a, b and c of a semiellipse to illustrate the measured volume formed by a light waveguide on illumination of a scattering tissue.

The measured volume can be determined approximately according to the invention from the determination of the detection depths in the x and z direction (see FIG. 15).

Assuming the measured volumes are semielliptical, the effective measured volume emerges according to FIG. 19 as:

$$V_{Meas.\ eff.} = \frac{2}{3}\pi abc$$

The determination quantities of the ellipse a, b and c can be found by calculating the effective depths of penetration from the intensity gradients. Because of the rotational symmetry of the illumination it is possible to set $$a = b = x_{eff},$$

the effective depth of penetration $x_{eff}$ in the lateral direction. The depth c can be determined from the effective depth of penetration in the transverse direction, and $$c = z_{eff}$$

is determined via the effective depth of penetration in the z direction, which is to be directed perpendicularly into the tissue. The 3 parameters of the semielliptical volume integral and thus the relevant measured volume are thus determined.

In the study by A. Krug [Krug, Thesis, Erlangen-Nuremberg University, 1998] it was proposed that the measured volume decreases as the absorber concentration increases. It is possible to show by correcting the measured backscattered extinctions by the reduced measured volume in each case that a linear relationship between the amount of absorber in the scattering suspension and the extinction relative to the current measured volume is obtained even with measurements in highly scattering media.

A method for determining the arterial oxygen saturation by means of a broad-band tissue spectrometer including all the spectral information is proposed according to the invention.

In a first approach, the arterial saturation of hemoglobin is determined by the usual pulse oximeter method with evaluation of at least two wavelengths, there being formation of a pulse-synchronous difference signal of the heart beat. These wavelengths should preferably be selected so that depth-selective determination of these arterial values is also possible, and so that the outputs of the monochromatic and of the broad-band light source are effective in an additive manner at these wavelengths. In a first approach, the conventional pulse oximeter method is included in the integrated sensor head.

A novel approach according to the invention is to determine the arterial saturation from the broad-band backscattered spectra of the tissue photometer. The tissue photometer allows the current hemoglobin saturation in the measured volume to be calculated via the method described above for determining the hemoglobin saturation. It is possible to detect the pulse-synchronous changes in saturation via a particularly rapid photometer whose scanning times in the region of 1–10 ms per value. The tissue photometer always detects an average appropriate for the volume-mixing ratio of arterial and capillary venous saturations.

According to the invention the arterial pulse is detected by laser Doppler signal evaluation and is used to trigger the tissue spectrometer.

The systolic blood pressure results in an increase in the blood flow and the blood volume in the tissue. In accordance with the theory of pulse oximetry, "fresh", completely saturated arterial blood is pushed into the tissue for this systolic increase in blood volume. This results also in total in a greater saturation of the blood in the measured volume of the tissue photometer. If, for the systolic blood volume addition, there is no determination of the diastolic blood volume and the saturation during systole and diastole it is possible with the rearranged mixing equation to determine the arterial saturations.

$$SO_{2\ Mix.syst.} \cdot Hb_{Amount_{Mix.syst.}} = SO_{2\ art.} \cdot \Delta Hb_{Amount_{art.}} + SO_{2\ Diast.} \cdot Hb_{Amount_{Diast.}}$$

$$SO_{2art} = \frac{SO_{2Syst.} \cdot Hb_{Amount_{Syst.}} - SO_{2Diast.} \cdot Hb_{Amount_{Diast.}}}{\Delta Hb_{Amount_{art.}}}$$

FIG. 20 shows two exemplary spectra. The 80% saturated spectrum corresponds to a state at the end of systole when the content of fresh oxygen-rich blood is greater than at the time of the period of the slower, diastolic perfusion during which the saturation essentially corresponds to the capillary venous saturation.

The blood volume $\Delta Hb_{amount,\ art.}$ is formed from the difference in the amounts of blood and hemoglobin at the end-systolic and end-diastolic time point. The method for hemoglobin determination as described above is used in this case too.

The saturations $SO_{2\ syst.}$ and $SO_{2\ diast.}$ are determined, likewise as described above, by evaluation of the curves of the tissue spectra.

However, the pulse oximeter method should also be determined from the spectrometric data set as pulse-synchronous difference signal in order to be able to draw valid conclusions owing to the greatly expanded spectral database. It is of particular interest to evaluate the difference signal of the spectrometric data because this difference signal can be related to the capillary venous baseline value and thus it is possible for the first time to determine a quantitative arterial oxygen saturation (see FIG. 20).

FIG. 20 shows two absorption spectra and their difference signal during the pulse-synchronous change in the spectra on the assumption of constant hemoglobin concentrations in the measured volume.

In another embodiment of the invention, a two-dimensional and a three-dimensional imaging of the local oxygen parameters (as shown in Table 1) by an imaging method is presented:

The description of the invention until now has related to point measurements in the vicinity of the illumination source, which consists either of a laser source, of LEDs or of a white light source.

However, in medicine, many imaging methods are in demand, starting with X-ray films, ultrasonic images and on to magnetic resonance images, which are very easily accessible to the trained eye of the physician. Information summarized in the form of images additionally provides an excellent possibility for transmitting a large amount of information with a high degree of order. A method for recording initially two-dimensional and subsequently three-dimensional images of the local distribution of the oxygen parameters which can be measured with the sensor described above is presented here.

The sensor technique for recording the various local oxygen parameters as listed in Table 1 has been explained in the preceding sections and is to serve as basis here. Differing from the sensor technique described above with point detection of the oxygen parameters, a novel, primarily two-dimensional imaging method is explained below.

Figure 21:
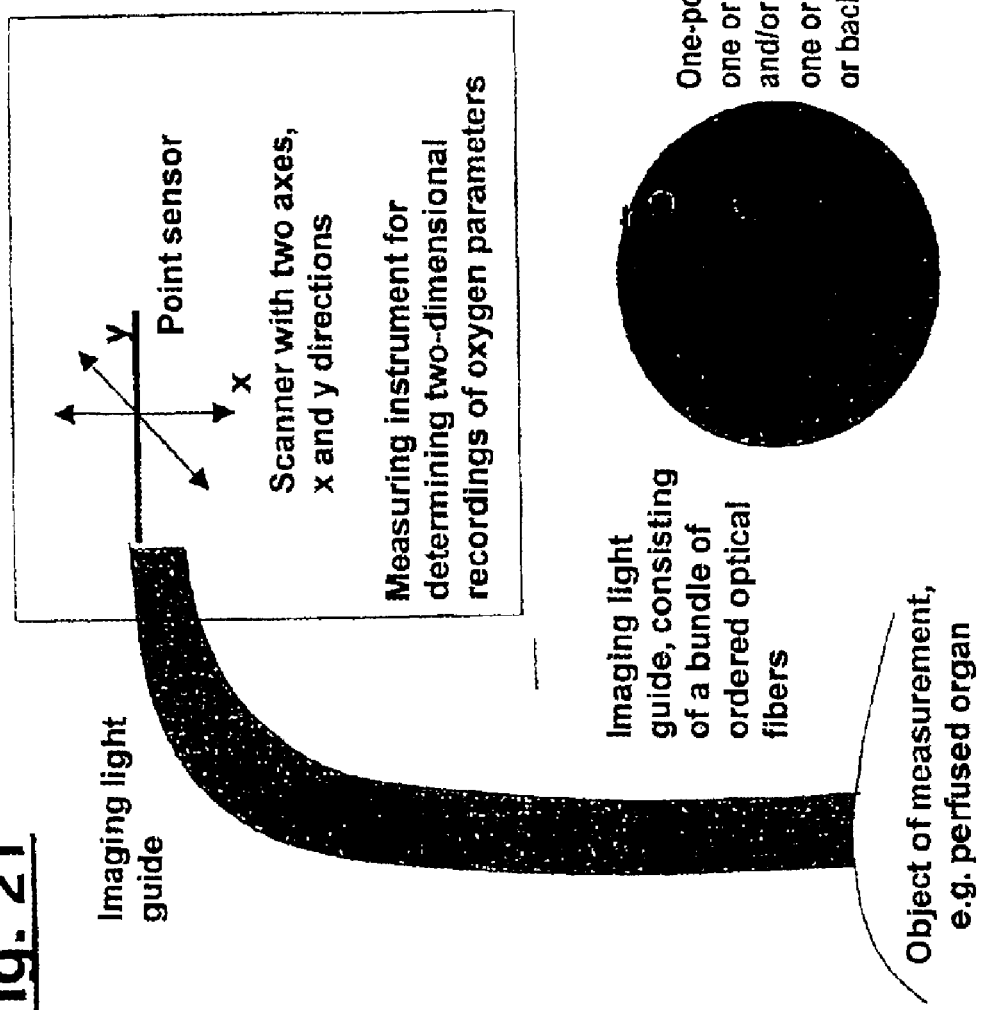

FIG. 21 shows the design in principle of the recording apparatus according to the invention for two-dimensional imaging of oxygen parameters. In this variant, the core of the sensor consists of an imaging light guide (also called imaging bundle) as already used in endoscopes or catheters in order to pass image information from the interior of the body to the outside. The imaging light guide is composed of a bundle of single fibers which are, however, arranged so that the image information is retained. This imaging light guide is arranged between the instrument and the measurement point on the object. In the measuring instrument, this imaging light guide is then scanned with the point measuring probe placed, as described above, directly on the object. The immense advantage of this arrangement derives from the fact that all the moving parts can be attached in the measuring instrument, and the sensor, in this case the end of the imaging light guide, can be fixed directly on the surface to be measured. The novel imaging sensor needs to be fixed only once. The scanning in the instrument means that the object is not displaced by the scanner movement itself, and it is now only necessary to scan the flat surface on the instrument side of the imaging light guide. This surface can be scanned with greater speed because the mechanical conditions therefor can be defined better in the instrument.

It is crucial that the individual fiber diameters in the imaging light guide are less than or equal to the cross sections of the point measuring probe. This ensures that the same sensor geometry is always produced by the imaging light guide as previously also defined directly by the point sensor. The imaging of the point sensor increases in accuracy as the density of the packing of the fibers increases and the thickness of the individual fibers of the imaging light guide decreases. The second alternative, exact 1:1 coupling of the individual fibers of the point sensor in each case into exactly one individual fiber of the imaging light guide is also possible but far more complicated.

It is also possible according to the invention to use a plurality of point sensors at the same time. This requires a multichannel illumination source and a multichannel detection unit. This makes it possible to reduce the time for a complete image because, if the point sensors are arranged side by side, for example in the y direction, it would then be necessary to carry out only half the number of scans in the x direction.

As an alternative to the imaging light guide, or as replacement for a scanner and the complete detection unit, it is also possible to use other cameras such as CCD cameras with an additional unit, which make direct spectral analysis of the detected information possible. These additions to the cameras have not to date made adequate spectral resolution possible, but this might soon be realized with further technical developments.

Figure 22:
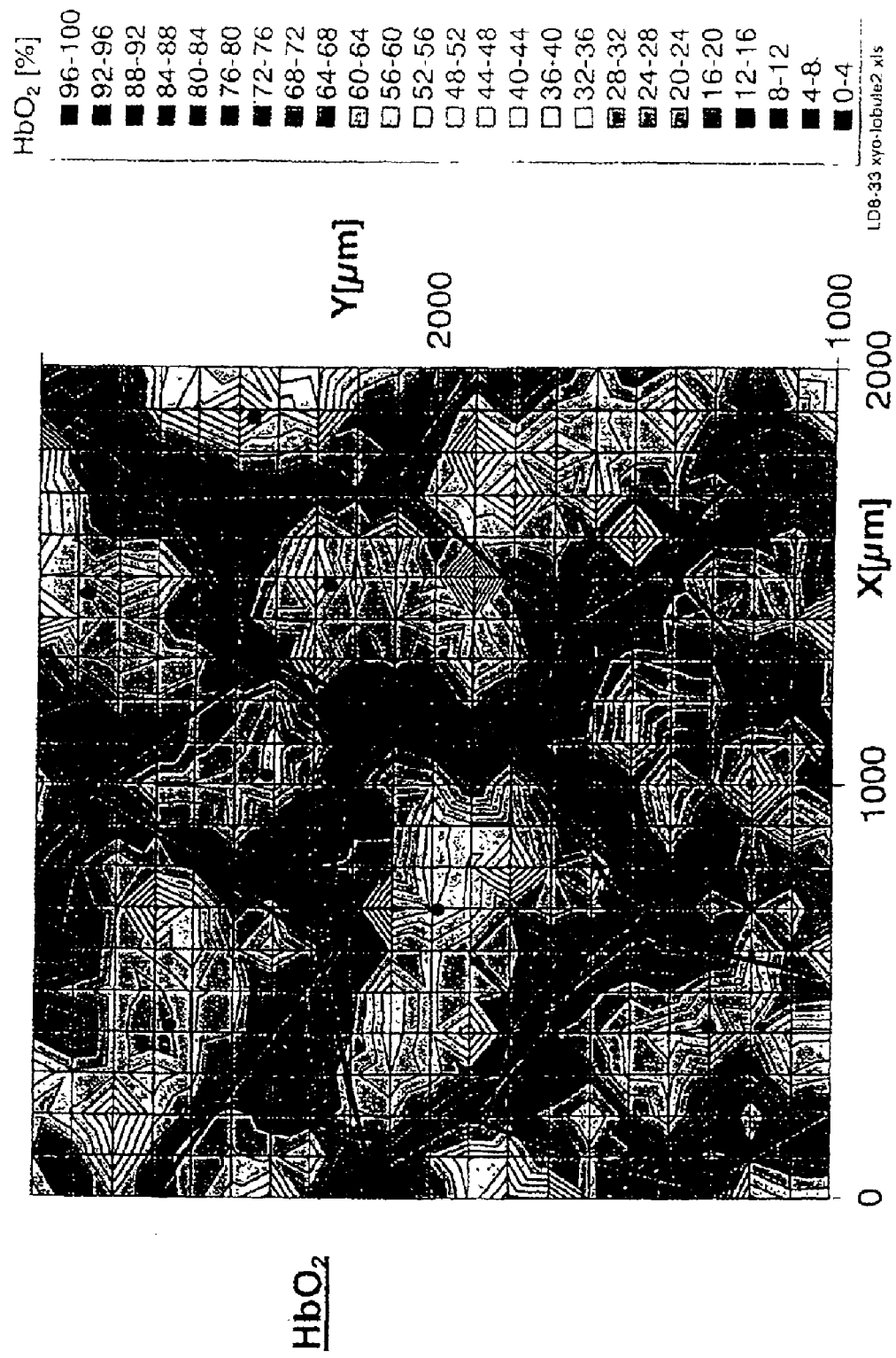

FIG. 22 shows the image of a scanned perfused liver surface, which demonstrates the local distribution of the hemoglobin saturation. In this method, which is still very elaborate, the point sensor was still advanced directly to the liver surface. Uncoupling of the movement of the point sensor from the organ surface was achieved by a PVC film stretched in between. The image is that of the distribution of the hemoglobin saturation on an isolated perfused liver surface. In accordance with the compilation of optical methods in Table 1, it is also possible to obtain images of the other oxygen parameters and the other tissue pigments mentioned in Table 3.

It emerged from these experiments that the sensor geometry is crucial for the spatial resolution with which the distribution of the oxygen parameters can be imaged. An appropriate sensor resolution appropriate for the morphological structure of the tissue which is to be investigated should therefore be selected via the fiber diameter, aperture and fiber material.

Figure 1:
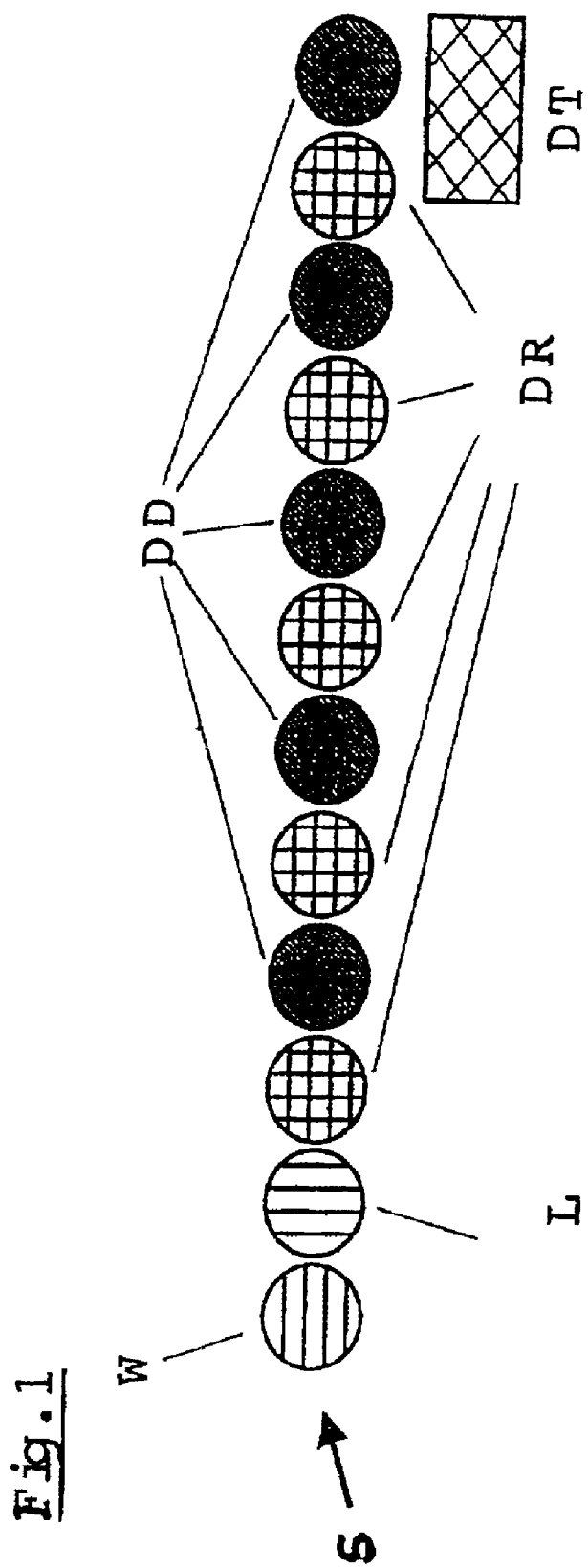
Figure 3:
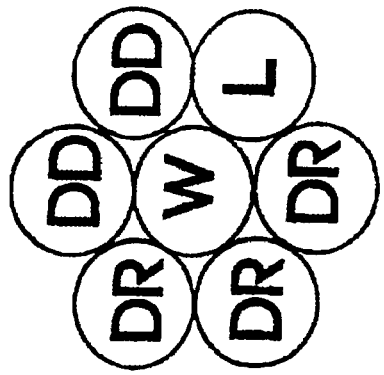
Figure 4:
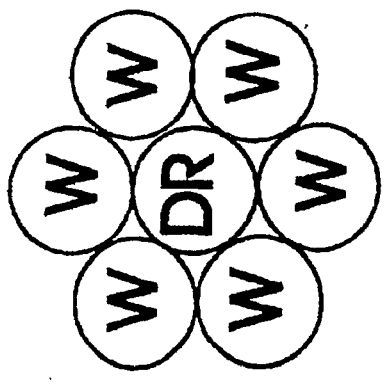
Figure 2:
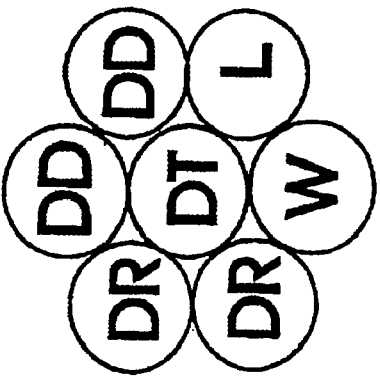
Figure 5:
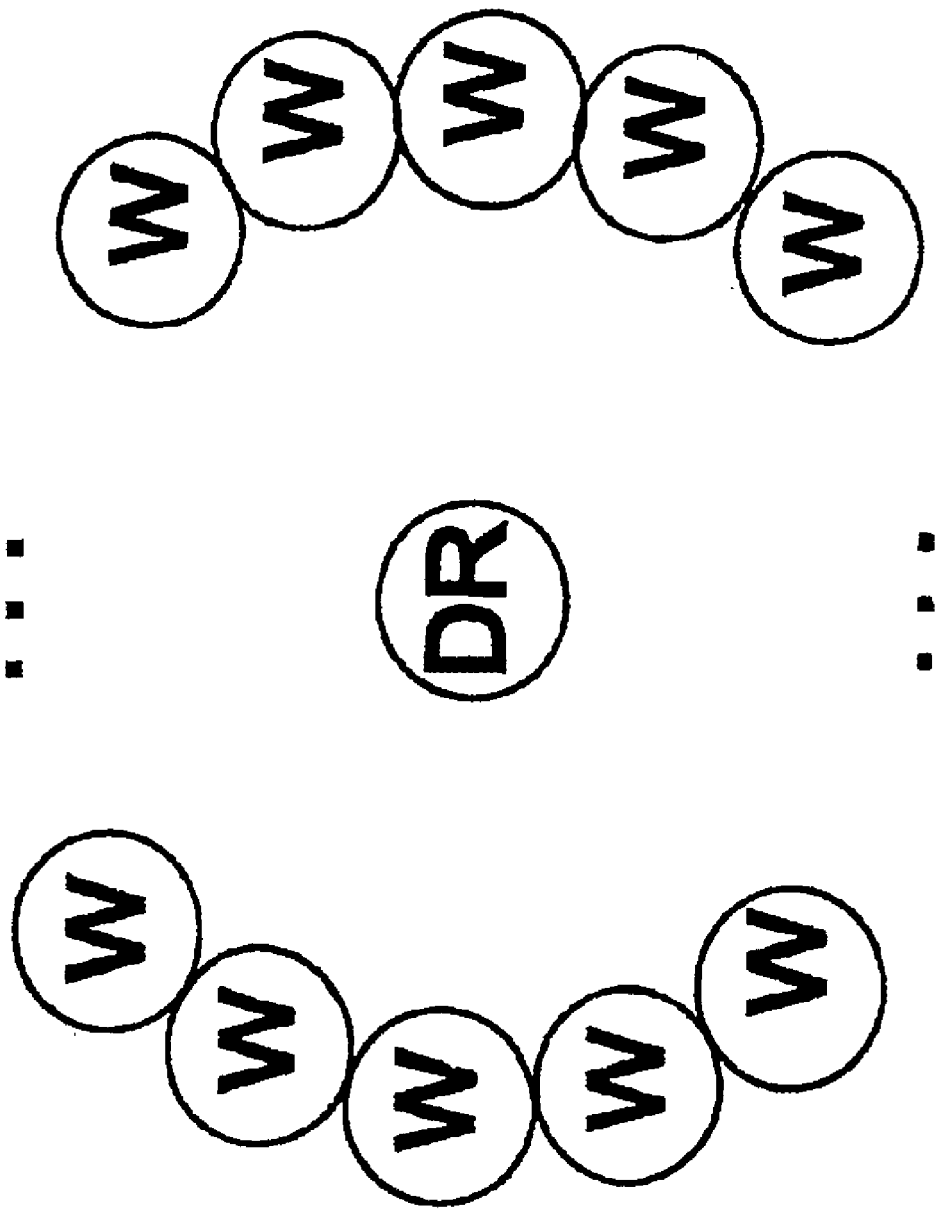
Figure 6:
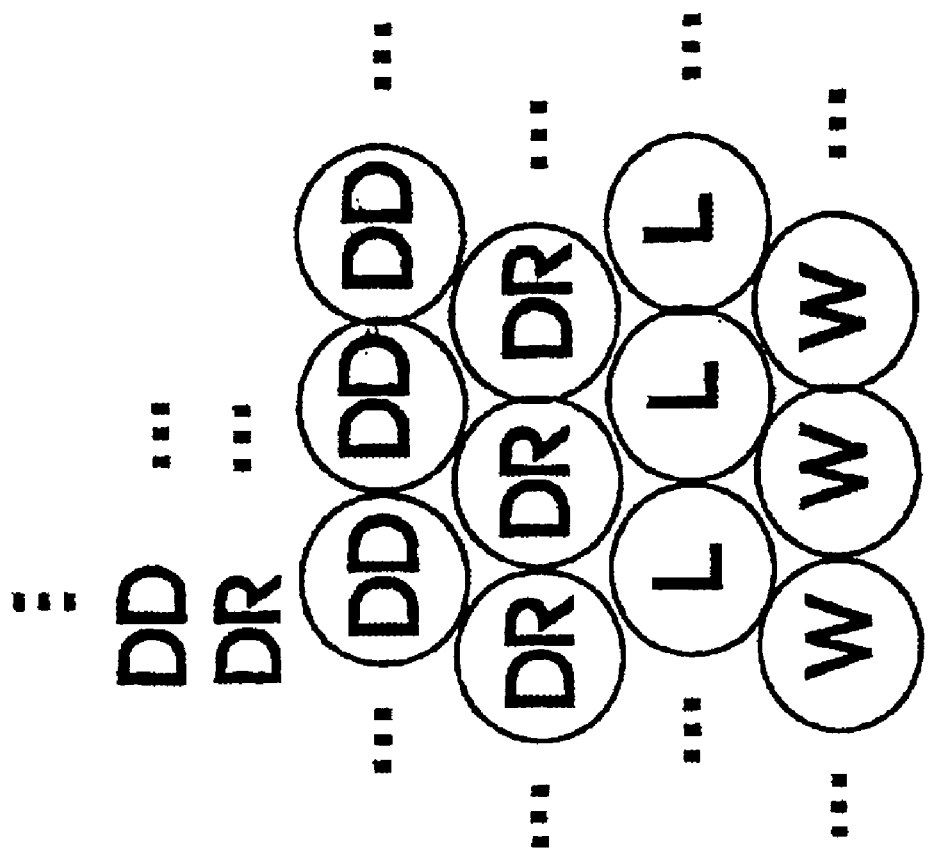
Figure 7:
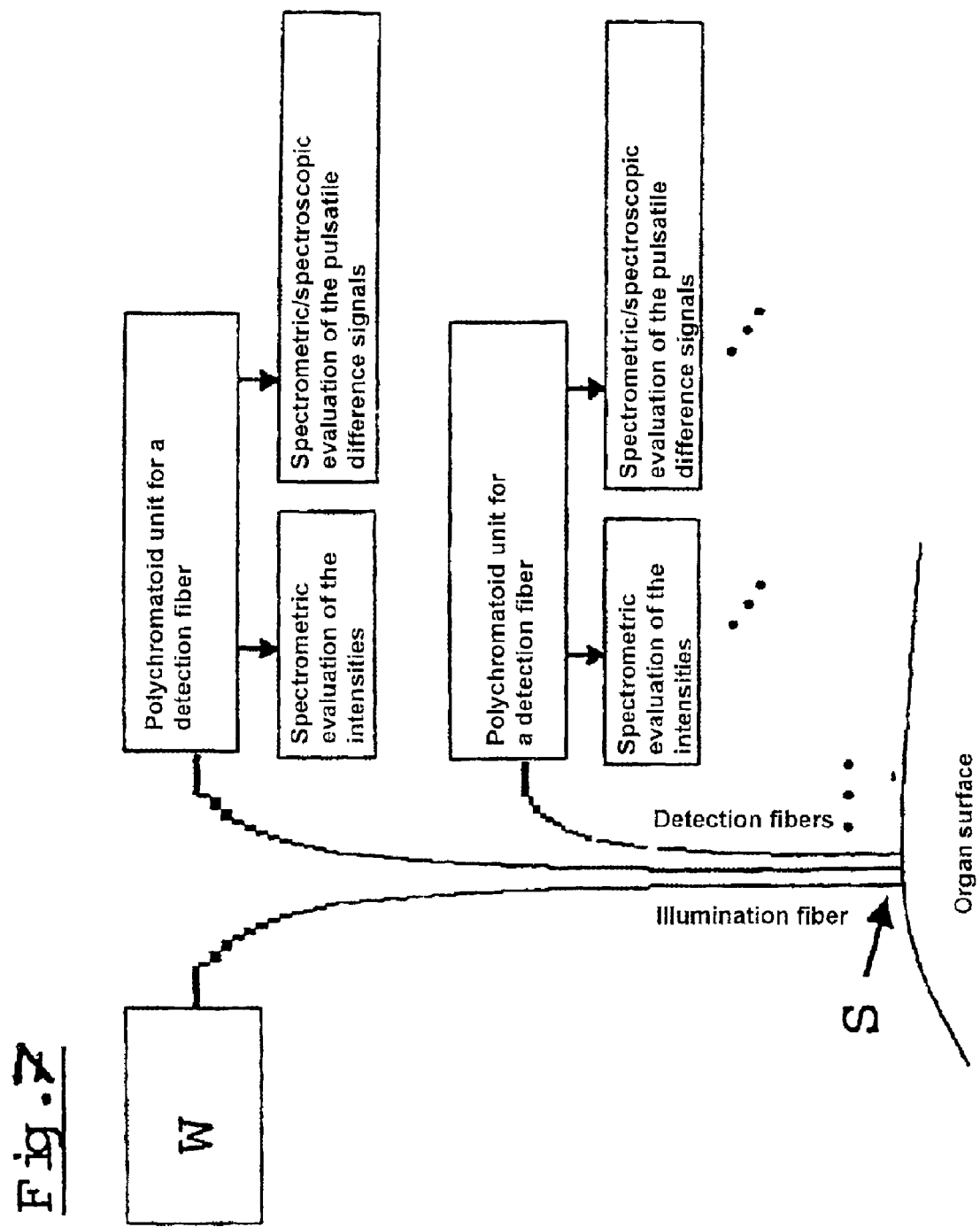
Figure 8:
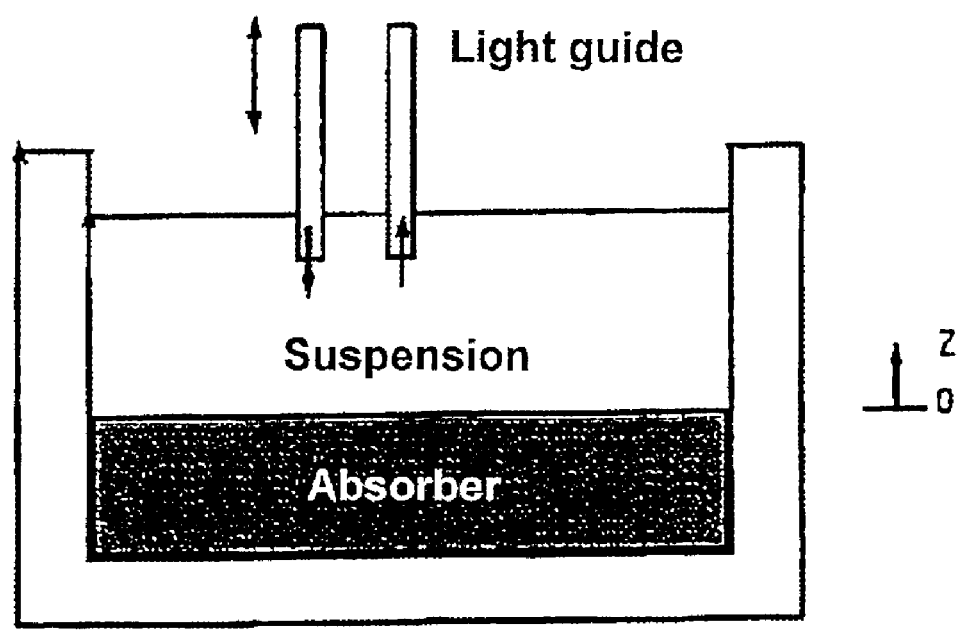
Figure 23:
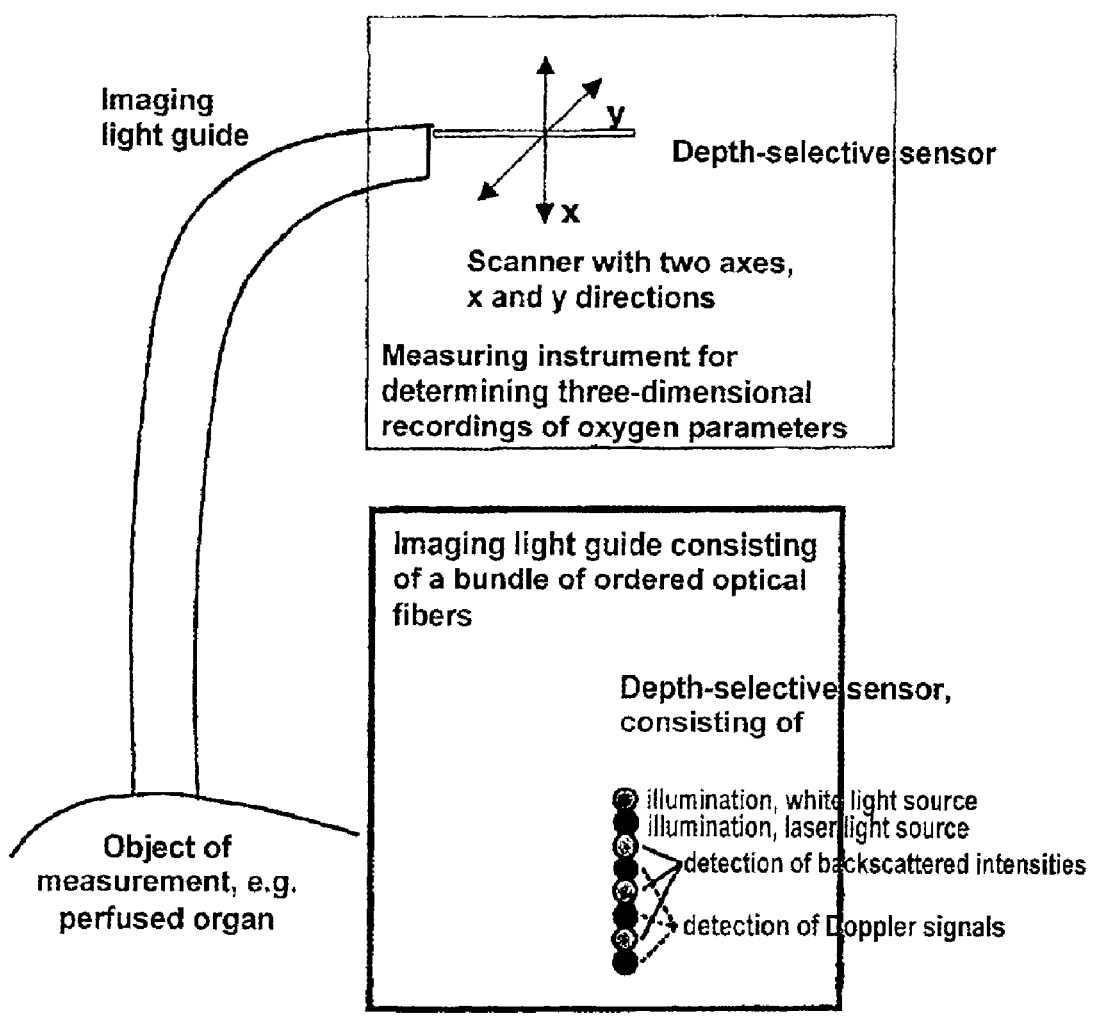

A three-dimensional recording method for imaging local oxygen parameters is built up on the two-dimensional recording method. As shown in FIG. 23, a similar type of imaging light guide (also called imaging bundle) as depicted in FIG. 21 is used. However, in contrast thereto the imaging light guide is now according to the invention scanned in the instrument with the depth-selective sensor from FIG. 1 with an x-y scanner. The two-dimensional imaging is combined with the depth-selective recording of the oxygen parameters via the sensor with a plurality of channels differing in separation both for the Doppler measurements and for the detection of the backscattered intensities.

One embodiment of the invention also permits determination of other tissue parameters with the spectrometric measurement methods described above:

Besides the chromophore hemoglobin, it is of interest to determine by spectrometry other pigments (summarized in Table 3) which occur in tissue, such as, for example, cytochromes, myoglobin, melanin and bilirubin.

Under physiological tissue conditions, measurements of other pigments at the same time as hemoglobin are very difficult because the absorption caused by the hemoglobin completely obliterates the spectra of the other pigments mentioned. However, determination of the tissue pigments mentioned in addition to hemoglobin is of physiological and clinical interest. Determination of the tissue pigments mentioned is possible in organs perfused free of hemoglobin or in pathologically altered situations. It is possible according to the invention to measure the redox state of the cytochromes, for example during organ transplantation, in the hemoglobin-free state. It is also possible to investigate the myoglobin oxygen saturation and concentration in skeletal and heart muscle.

The methods for producing 2-dimensional and 3-dimensional images of the oxygen parameters shown in Table 1 and/or of the derived parameters shown in Table 3, obtained from tissue levels through combination of the signals from the tissue spectrometer and/or the laser Doppler and/or the pulse oximeter and/or temperature sensor are novel, especially in their combination of the methods.

Figure 24:
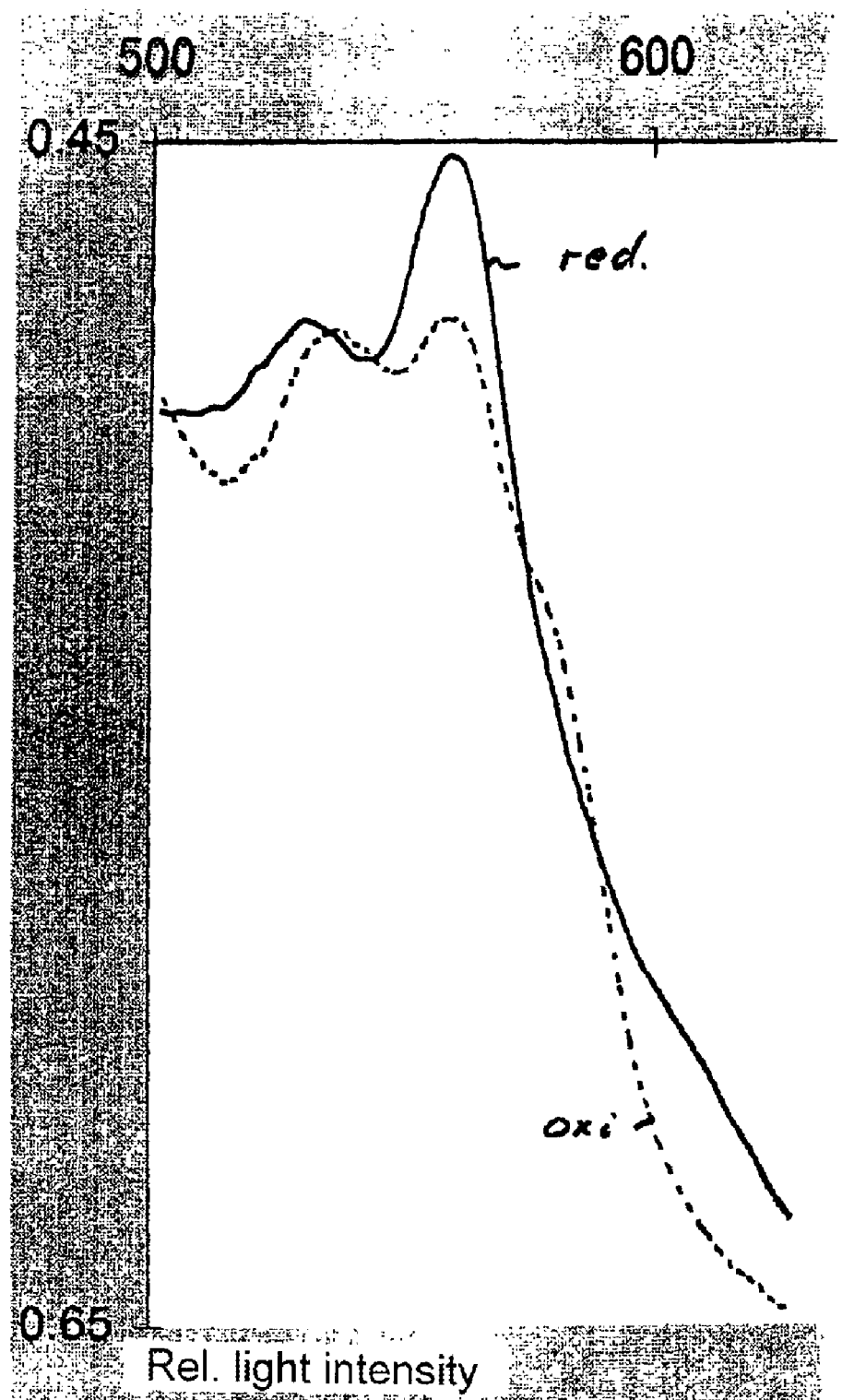

The importance of monitoring these tissue substances is that this opens up the possibility of being able to investigate directly the intracellular oxygen supply conditions. The Fitt algorithm described above can be converted to calculation of the redox state of the cytochromes investigated by providing completely reduced and completely oxidized cytochrome reference spectra (see FIG. 24). FIG. 24 shows cytochrome spectra, oxidized cytochromes and reduced cytochromes, measured in mitochondrial suspension.

It is possible in the same way, by providing completely oxygenated and completely deoxygenated myoglobin spectra, also to calculate the myoglobin saturation with oxygen via the Fitt algorithm described above.

The spectral method according to the invention for determining the hemoglobin concentration from backscattered spectra can be applied in a similar way for the tissue pigments mentioned herein for determining the intracellular cytochrome, myoglobin, melanin and bilirubin concentrations.

The wavelength range from 500 to 650 nm is particularly suitable for determining the cytochrome and myoglobin levels with abovementioned methods because, in this wavelength range, the naturally low absorption coefficients of these cellular absorbers have the comparatively highest values. It is thus possible in this wavelength range to attain the clearest absorption spectra with the best signal-to-noise ratio.

Melanin, the skin pigment, and bilirubin, a hemoglobin breakdown product, have less characteristic spectral curve shapes than do the cytochromes. Myoglobin and hemoglobin can therefore be measured quantitatively only less specifically and less unambiguously.

The method for determining concentrations of an absorber present in the tissue can, of course, also be extended to artificially injected dyes. It is thus possible for color influx and efflux curves to be measured noninvasively and locally in the tissue directly.

TABLE 3

Pigments and/or pigment concentrations which naturally occur in the tissue and/or are introduced into the tissue and which can be determined with the tissue spectrometer using the methods according to the invention

| Pigment | Determination parameter | Method |
| --- | --- | --- |
| Hemoglobin | Oxygen saturation | Fitt algorithm, with reference spectra |
|  | Hemoglobin concentration | Area integration method with tissue normalization |
| Cytochromes | Redox state | Fitt algorithm, with reference spectra |
|  | Intracellular cytochrome concentration | Area integration method with tissue normalization |
| Myoglobin | Myoglobin oxygenation | Fitt algorithm, with reference spectra |
|  | Intracellular myoglobin concentration | Area integration method with tissue normalization |
| Melanin | Melanin concentration | Absorption determination |
| Bilirubin | Bilirubin concentration | Absorption determination |
| Artificial dyes | Specific dye concentration | Absorption determination |
|  | Permeability tests | Color efflux method |

It is thus possible and preferable to carry out the following measurements and calculations with the apparatus according to the invention:

To determine the oxygen content, only the output signals of the broad-band tissue backscattering spectrometer are evaluated. The oxygen saturation ($SO_2$) is determined from the tissue spectra via the color information, and the hemoglobin concentration ($Hb_{conc.}$) is determined from the attenuation of light. The tissue levels can be measured depth-selectively by the multichannel tissue spectrometer signals measuring at various separations, and be related to the relevant measured volume, which is determined on line. Multichannel spectrometer measurement is crucial because this measuring configuration allows the $SO_2$ values and/or the $Hb_{conc.}$ values to be related to the measured volume. The measured volume is determined by gradient measurements and subsequent determination of absorption and scattering. Measurements at the same site and time through the same sensor (see FIG. 1) are crucial in order to be able to ensure relation of the signals to the particular measured volumes.

To determine the oxygen consumption in arterial/venous mixed tissue, the output signals of the tissue spectrometer are in evaluated together with the pulsatile signals either from a pulse oximeter or from a fast tissue spectrometer. In the case of pulsatile tissue spectrometer measurement, the largest saturation values are evaluated differentially during a cardiac cycle in order to be able to discriminate only the arterial blood contribution. The high data acquisition rate is crucial in order to be able to detect the arterial circulation pulse. Without discrimination of the pulse it is impossible to determine any arterial $O_2$ saturation. Triggering of the measurement time point for the arterial determination is defined from the laser Doppler signals and/or the time-resolved signals of the $Hb_{conc.}$ determination. This innovative calculation method for determining the arterial saturation is based on evaluation of the signals from a fast broad-band tissue spectrometer (<20 ms per clock period) and/or the triggering via the signal of the laser Doppler unit.

Measurements at the same site and time through the same sensor (see FIG. 1) are crucial in order to be able to ensure relation of the signals to the particular measured volumes.

The total amount of blood, also referred to as the total amount of tissue hemoglobin, is determined by evaluation of the multichannel tissue spectrometer signals which are carried out at the same time at different separations. The hemoglobin concentration relative to the measured volume is determined from the broad-band tissue backscattering spectra. The total amount of blood in the measured volume is established therefrom by including the laboratory parameters of the hematocrit and the mean corpuscular hemoglobin.

The oxygen transport capacity is determined from the output signals from the multichannel tissue spectrometer measurement and the hemoglobin concentration signal, together with the blood flow output signal of the laser Doppler method. Measurements at the same site and time through the same sensor (see FIG. 1) are crucial in order to be able to ensure relation of the signals to the particular measured volumes. It is important to employ the two methods together in order to be able to determine the oxygen transport capacity. The blood flow on its own is insufficient to allow any statement about the hemoglobin content of the erythrocytes and thus also about the oxygen binding and transport capacity. The hemoglobin concentration on its own in turn provides no information about the movement or velocity of the erythrocytes.

To determine the locally transported amount of oxygen, once again multichannel output signals from the tissue spectrometer, the oxygen saturation signal, the hemoglobin concentration, the output signals from the laser Doppler and the blood flow rate or the blood flow must be combined together in order to achieve maximum accuracy. Determination at the same site and time of the tissue spectrometer signals and the laser Doppler signals through the same probe in measured volumes which are thus comparable is crucial for obtaining these signals. Measurements at the same site and time through the same sensor (see FIG. 1) are crucial in order to be able to ensure relation of the signals to the particular measured volumes.

The oxygen consumption rate in arterial/venous mixed tissue is a relative numerical measure dispensing with an absolute relation of the $Hb_{conc}$ and $SO_2$ to the measured volume. It is therefore possible in this case also to carry out single channel spectrometer and pulse oximeter measurements. The output signals of the tissue spectrometer ($SO_2$ and $Hb_{conc}$) and the pulse oximeter signals or the pulsatile differential output signals of the tissue spectrometer (arterial $SO_2$) are combined and evaluated synchronously. Measurements at the same site and time through the same sensor (see FIG. 1) are crucial in order to be able to ensure relation of the signals to the particular measured volumes.

To determine the oxygen turnover, the primary signals of the broad-band tissue spectrometer ($SO_2$ and $Hb_{amount}$) of the pulsatile tissue spectrometer, of the pulse oximeter ($SO_{2\ art.}$) and/or the laser Doppler primary signals ($v_{blood}$, $Amount_{erys,\ moving}$) are evaluated in a multichannel manner in order to be able to achieve the relation to the measured volume and/or the depth selectivity of the values. The oxygen turnover indicates the difference in the volumetric flow of $O_2$ delivered arterially and transported away venously. Measurements at the same site and time through the same sensor (see FIG. 1) are crucial in order to be able to ensure relation of the signals to the particular measured volumes. In addition, determination of the measured volume through spectral intensity gradients is crucial for relating the numerical measure of amount to the joint measured volume.

To determine the oxygen turnover rate in arterial/venous mixed tissue, the quantitative relation to the measured volume is dispensed with. Also necessary for this purpose are single channel or multichannel tissue spectrometer signals ($SO_2$) and single channel or multichannel pulsatile tissue spectrometer signals and/or pulse oximeter signals ($SO_{2\ art.}$) and single channel or multichannel laser Doppler signals (blood flow) for calculating the oxygen turnover rate.

To determine the local tissue oxygen partial pressure ($pO_2$) it is necessary to determine at the same site and time the primary signals of the tissue spectrometer ($SO_2$) and the temperature (T), and the laboratory parameters ($pCO_2$ and 2, 3 BPG). The local $PO_2$ can be approximately determined for capillary venous and/or arterially supplied tissue by discrimination of capillary venous $SO_2$ and arterial $SO_{2\ art.}$.

Figure 9:
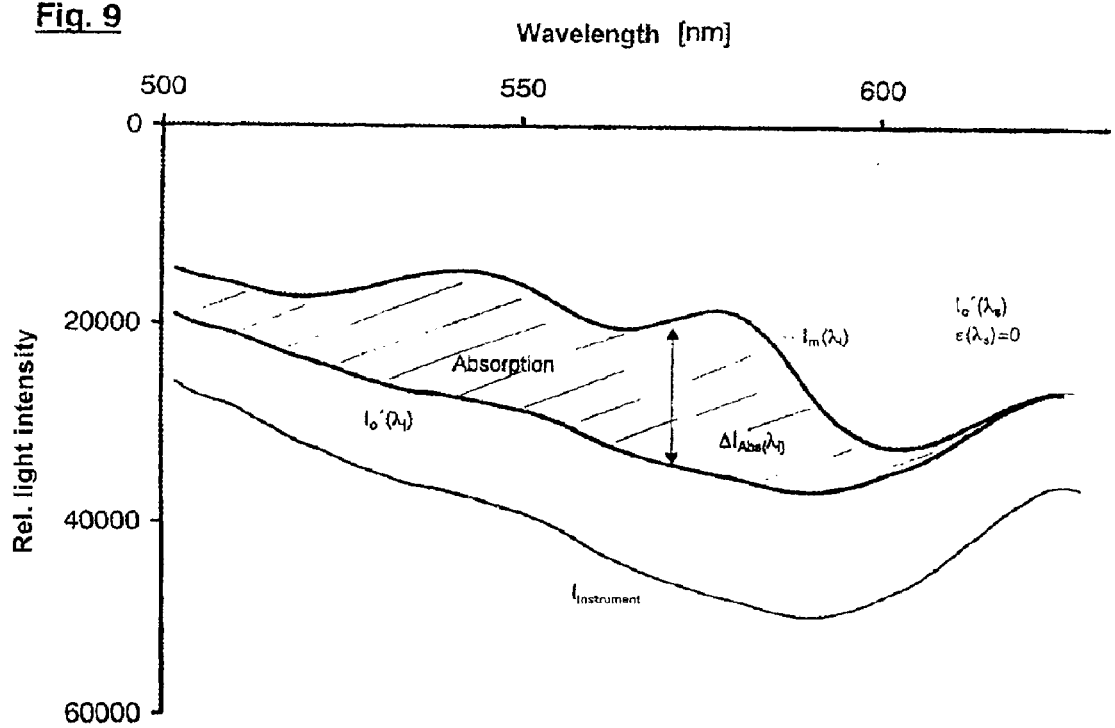
Figure 10:
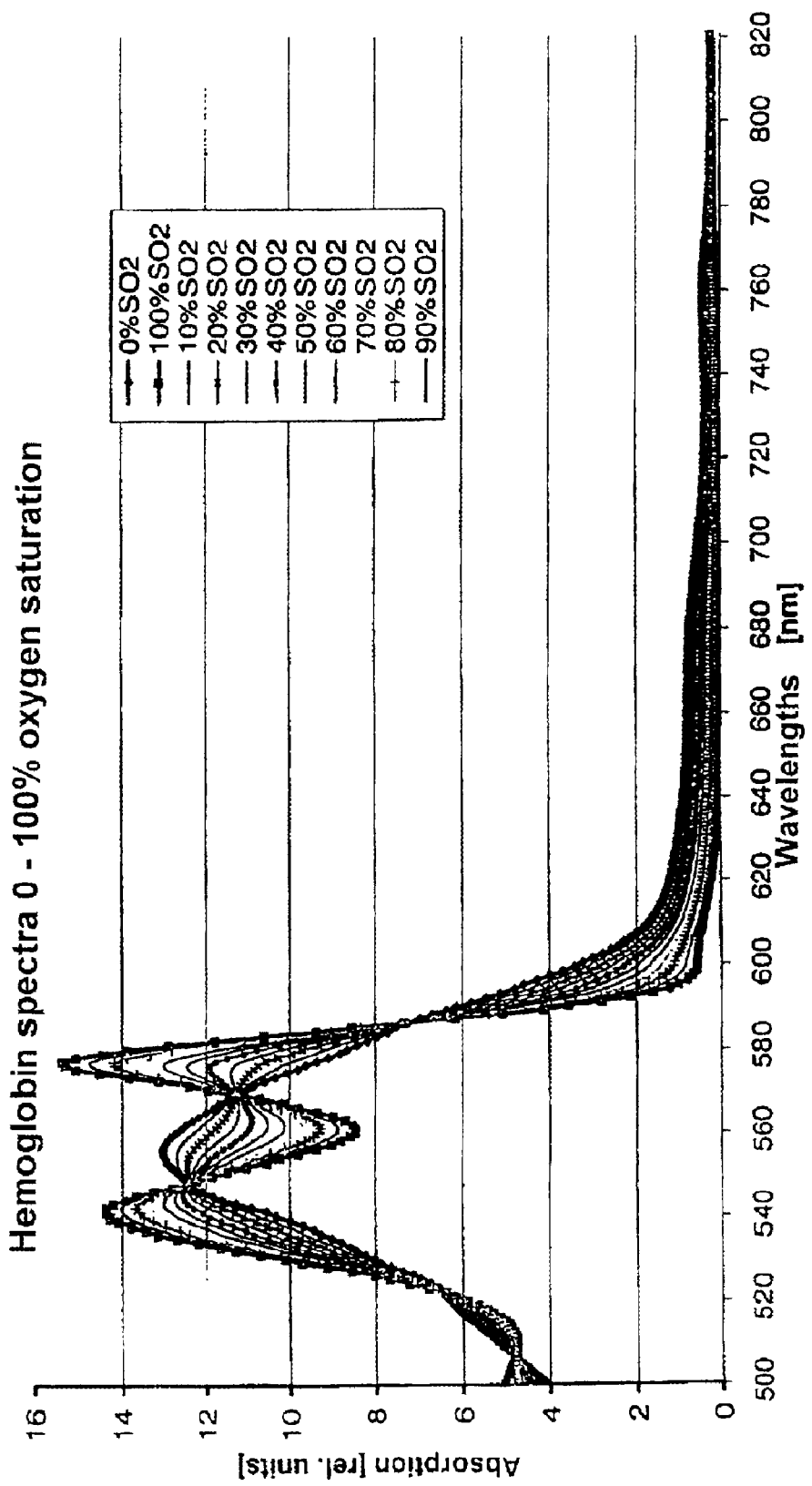
Figure 11:
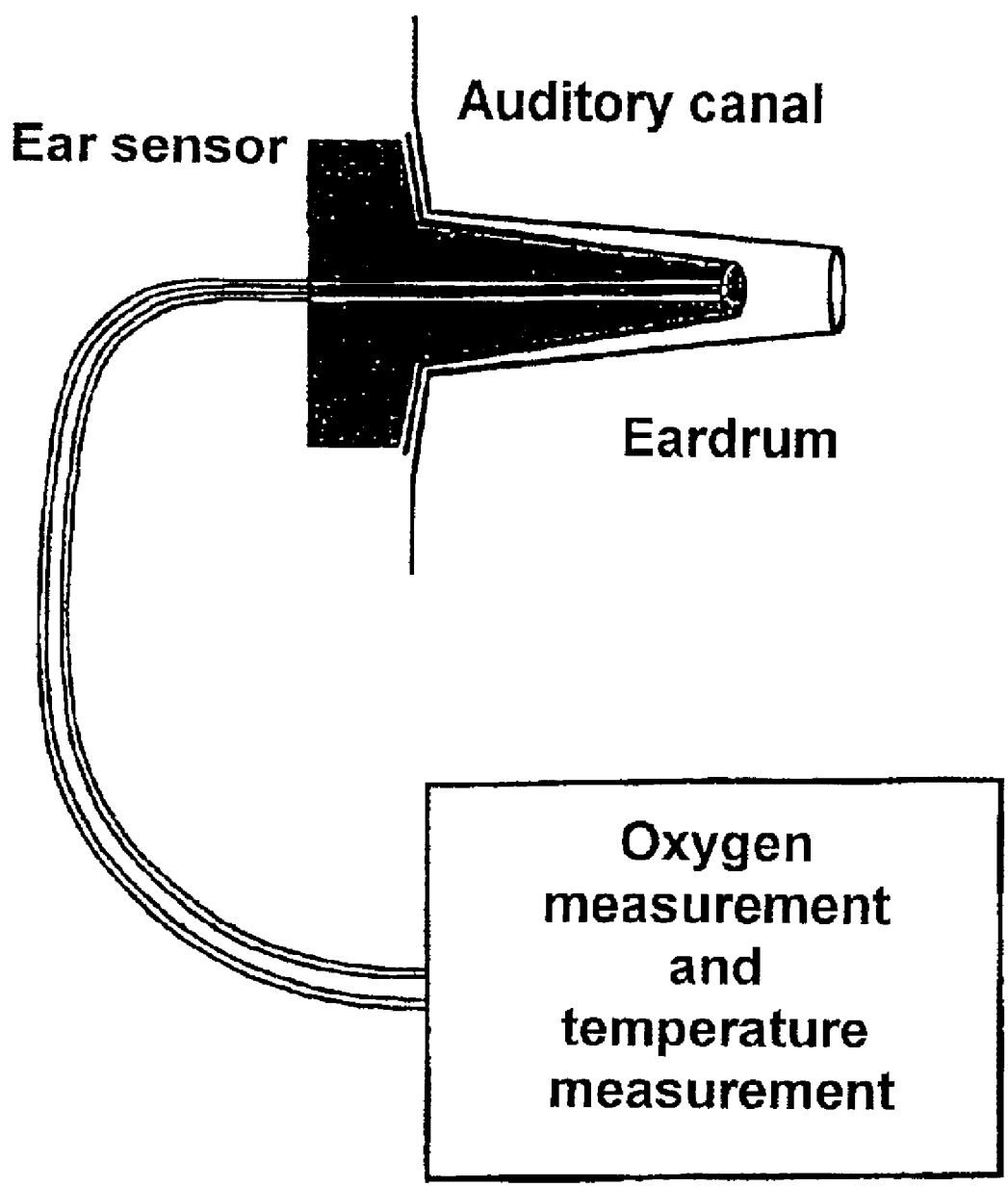
Figure 12:
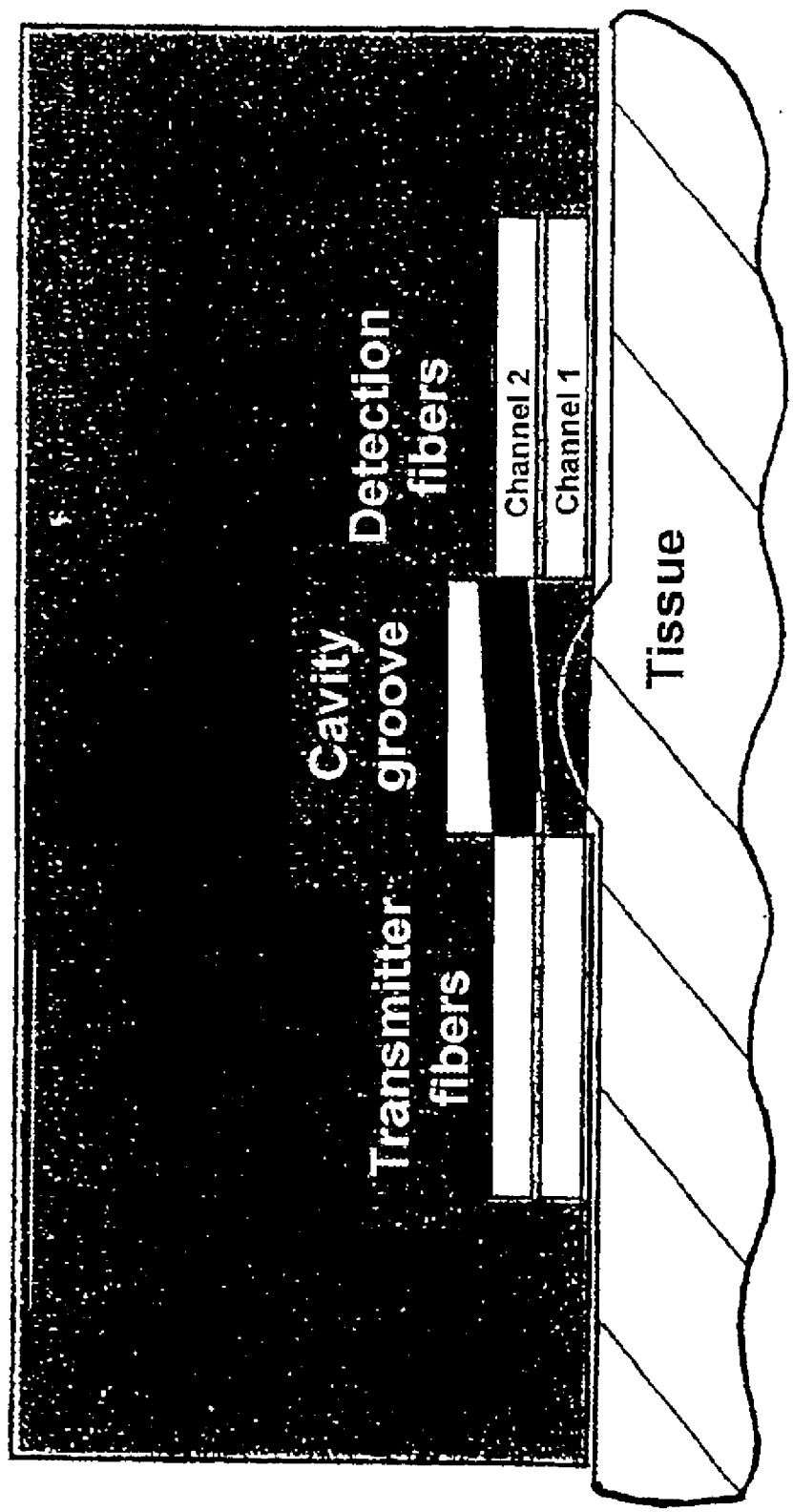

The method for determining the local hemoglobin concentration from tissue spectra is also according to the invention. This is normalized to the approximated basic tissue spectrum as shown in FIG. 9 with, at the same time, the $Hb_{amount}$, which is calculated from the extracted Hb amplitudes, being related to the relevant measured volume of the sensor. The measured volume was determined from light intensity gradients which are evaluated spectrally in order to determine therefrom the transfer function as shown in FIG. 24 and/or the absorption and scattering coefficients of all the wavelengths involved from the diffusion theory, to which the $Hb_{amount}$ value is related.

Methods for determining the arterial oxygen saturation by differential evaluation of the time-resolved spectral backscattered signals as shown in FIG. 20 with the aid of a fast broad-band tissue spectrometry are also according to the invention. It is also possible to combine with a laser Doppler system for triggering the arterial flow pulse time point for determining the oxygen saturation with the largest, that is to say arterial, saturation contribution. The advantage of this combination is that the spectrum recording rate of the tissue spectrometer now necessary is thus only relatively low.

What is claimed is:

1. An apparatus for ascertaining the local oxygen turnover and/or the oxygen consumption and/or the $O_2$, transport capacity and/or the transported $O_2$ amount and/or the oxygen consumption rate and/or the oxygen turnover rate and/or the oxygen turnover rate and/or data derived from the content of tissue pigments, ascertained from the primary signals of the local hemoglobin concentration and/or the content of tissue pigments and/or the local oxygen saturation and/or the arterial oxygen saturation and/or the blood flow rate and/or the transported amount of blood and/or the tissue temperature with an optical sensor (S) for placing on the tissue, characterized by at least one white light source (W) and at least one laser source (L) which send light to the sensor (S), one or more detectors (DD, DR) which receive light backscattered from the tissue, and an evaluation unit, and characterized in that optical fibers are provided between light sources (W, L) and sensor (S) and between sensor (S) and detectors (DD, DR), with the optical fibers of the sensor (S) preferably being arranged on a circular shape around a central fiber or a temperature probe (DT), and in that one fiber each for the white light source (W) and for the laser (L), and in each case at least two detection fibers (DR, DD) lie on an arc of a circle at defined distances from the illumination sources, each of which is fed to a separate evaluation.

2. The apparatus as claimed in claim 1, characterized in that a spectrometer, a spectroscope, a laser Doppler spectroscope, a tissue spectrometer, a tissue spectroscope and/or a pulse oximeter and/or a temperature measurement (DT) ore provided as evaluation unit.

3. The apparatus as claimed in claim 1, characterized in that the primary signals are related to a optically determined measured volume and/or in that the measured volume of the optical sensor is determined and information is obtained from various depths by evaluation of the various wavelength ranges and at least one detector-transmitter separation.

4. The apparatus as claimed in claim 1, characterised in that the detection fibers (DR) are evaluated together.

5. The apparatus as claimed in claim 1, characterized by a bundle of optical fibers which extends from the sensor (S) to the detector or to a camera, such as a color CCD camera, so that a two-dimensional imago of the evaluated signals can be generated.

6. An oxygen sensor as set forth in claim 1 for measurements on the eardrum, in which the primary signals of the tissue spectrometer ($SO_2$, $HB_{amount}$)) and/or of the pulsatile tissue spectrometer and/or of the pulse oximeter ($SO_{2\ art}$) and/or of the laser Doppler (blood flow) are recorded in a reflection measurement and combined with one another in order to be able to determine the oxygen parameters and/or the pigment parameters via the ear sensor.

7. The apparatus as claimed in claim 1, characterized in that the fibers with a separation $x_i$ are illuminated and/or evaluated together.

8. The apparatus as claimed in claim 1, characterized in that a pressure indicator signal in generated via opposing light guides and/or light exit and entry regions and indicates the deformation of the tissue and/or of a membrane because of application of the sensor.

9. The apparatus for ascertaining the local oxygen turnover and/or the oxygen consumption and/or the $O_2$ transport capacity and/or the transported $O_2$ amount and/or the oxygen consumption rate and/or the oxygen turnover rate and/or the oxygen turnover rate and/or data derived from the content of tissue pigments, ascertained from the primary signals of the local hemoglobin concentration and/or the content of tissue pigments and/or the local oxygen saturation and/or the arterial oxygen saturation and/or the blood flow rate and/or the transported amount of blood and/ar the tissue temperature with an optical sensor (s) for placing on the tissue, characterized by at least one white light source (W) and at least one laser source (L) which send light to the sensor (S), one or more detectors (DD, DR) which receive light backscattered from the tissue, and an evaluation unit, and characterized in that the illuminated fibers for a white light source and/or a laser light source lie on an open or closed are of a circle directly around the central fiber and are illuminated by one or more light sources, with detection of the backscattered and/or laser Doppler signals taking place through the central fiber.

10. The apparatus as claimed in claim 9, characterized in that the illuminated fibers (W) and/or (L) lie on a larger radius and/or on different radii of a circle which are illuminated synchronously and/or alternately.

11. An apparatus for ascertaining the local oxygen turnover and/or the oxygen consumption and/or the $O_2$ transport capacity and/or the transported $O_2$ amount and/or the oxygen consumption rate and/or the oxygen turnover rate and/or the oxygen turnover rate and/or data derived from the content of tissue pigments, ascertained from the primary signals of the local hemoglobin concentration and/or the content of tissue pigments and/or the local oxygen saturation and/or the arterial oxygen saturation and/or the blood flow rate sensor the transported amount of blood and/or the tissue temperature with an optical sensor (S) for placing on the tissue, characterized by at least one white light source (W) and at least one laser source (L) which send light to the sensor (S), one or more detectors (DD, DR) which receive light backscattered from the tissues and an evaluation unit, characterized by a bundle of optical fiber, which extends from the sensor (S) to the detector or to a camera, such as a color CCD camera, so that a two-dimensional image of the evaluated signals can be generated, and characterized by an additionally depth-selective sensor (S) or a depth-selective evaluation so that a three-dimensional image of the recorded measurements can be generated.

* * * * *